United States Patent [19]

Shu et al.

[11] 4,234,616
[45] Nov. 18, 1980

[54] FLAVORING WITH MIXTURES OF 2,5-DIALKYL DIHYDROFURANONES AND 2,4,5-TRIALKYL DIHYDROFURANONES

[75] Inventors: Chi-Kuen Shu, Cliffwood; Braja D. Mookherjee, Holmdel; Manfred H. Vock, Locust, all of N.J.

[73] Assignee: International Flavors & Fragrances Inc., New York, N.Y.

[21] Appl. No.: 63,561

[22] Filed: Aug. 3, 1979

Related U.S. Application Data

[63] Continuation-in-part of Ser. No. 928,606, Jul. 27, 1978, abandoned.

[51] Int. Cl.³ .............................................. A23L 1/226
[52] U.S. Cl. .................................. 426/536; 260/347.8
[58] Field of Search ...................... 426/536; 260/347.8

[56] References Cited

U.S. PATENT DOCUMENTS

| 3,980,675 | 9/1976 | Venturello et al. ............... 260/347.8 |
| 4,127,592 | 11/1978 | Cohen ............................. 260/347.8 |

FOREIGN PATENT DOCUMENTS

| 2359891 | 6/1974 | Fed. Rep. of Germany ........ 260/347.8 |
| 1440270 | 6/1976 | United Kingdom . |

*Primary Examiner*—Joseph M. Golian
*Attorney, Agent, or Firm*—Arthur L. Liberman

[57] ABSTRACT

Described are the novel compounds having the structures:

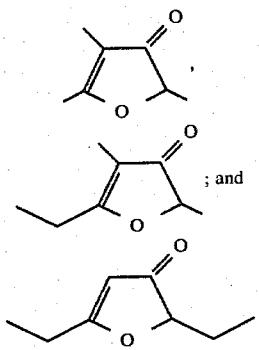

; and and mixtures of same taken together with 2-ethyl-5-methyl dihydrofuranone which has the structure:

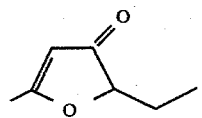

for use in augmenting or enhancing the sweet, brown sugar, pineapple-like, caramel, buttery, scorched butter-like, dried hazelnut and earthy aroma and sweet, brown sugar, pineapple-like, caramel, buttery, cheese-like, roasted, vanilla-like, dried hazelnut and earthy tastes of foodstuffs and of foodstuff flavoring compositions.

2 Claims, 17 Drawing Figures

GC PROFILE, FOR EXAMPLE I.

NMR SPECTRUM FOR EXAMPLE I.

FIG. 3 NMR SPECTRUM FOR EXAMPLE I.

NMR SPECTRUM FOR EXAMPLE I

NMR SPECTRUM FOR EXAMPLE I.

FIG.6 IR SPECTRUM FOR EXAMPLE I

FIG. 8 IR SPECTRUM FOR EXAMPLE I

FIG. 9 IR SPECTRUM FOR EXAMPLE I

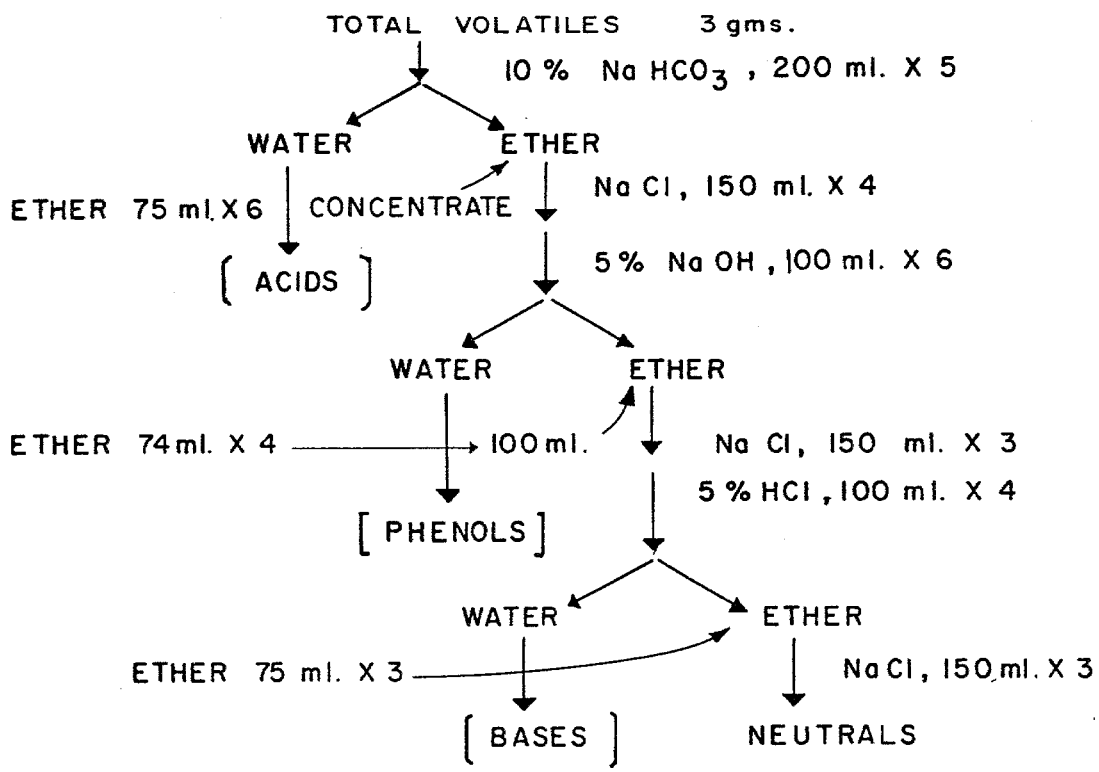
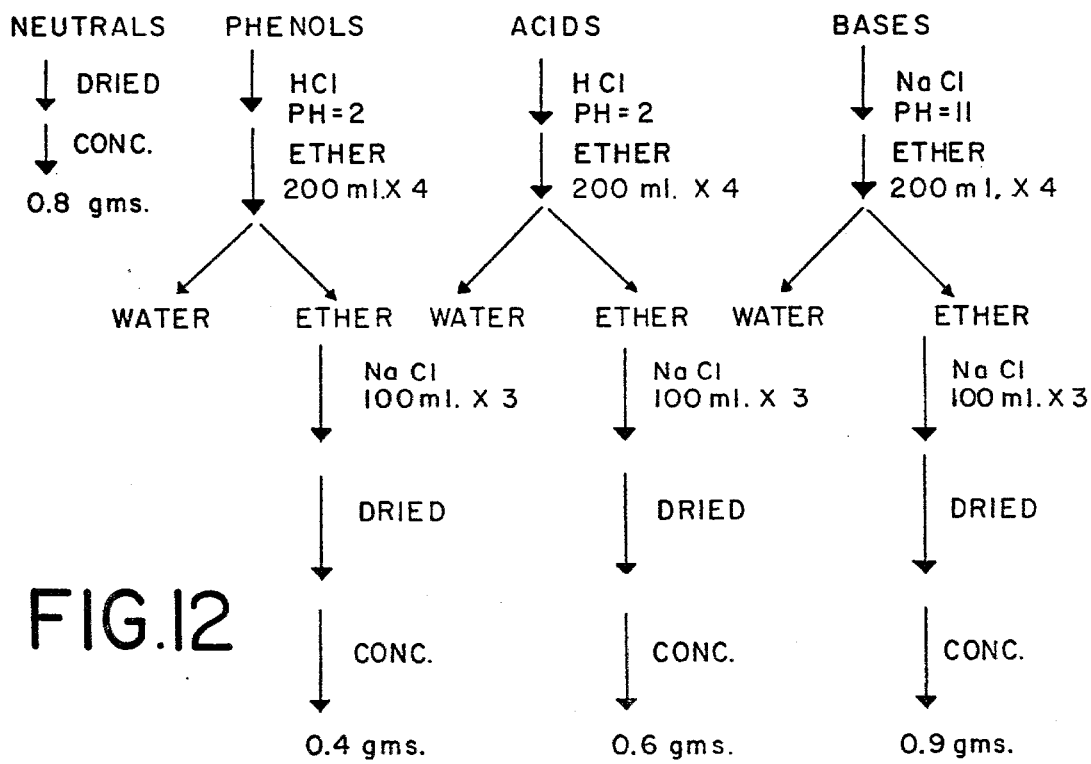
FIG.12

GLC PROFILE

SYNTHESIZED

IR SPECTRUM

NMR SPECTRUM

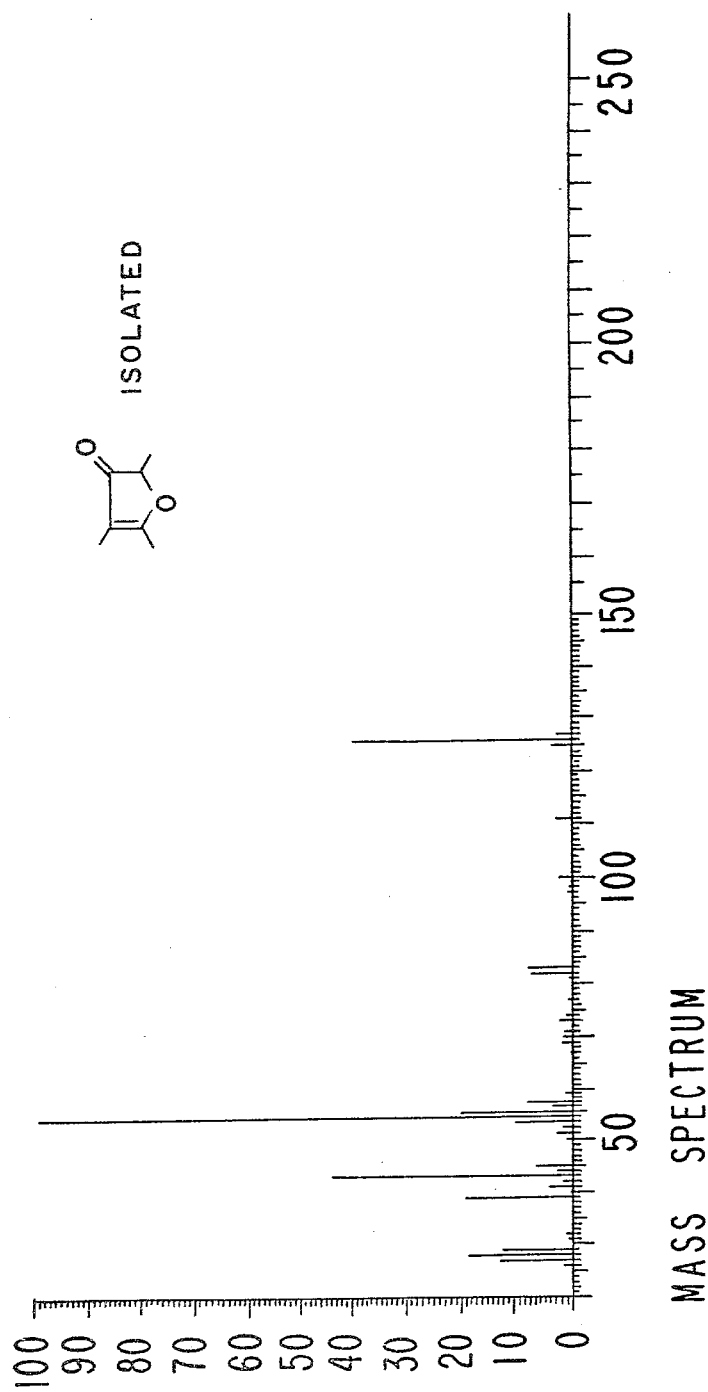

FLAVORING WITH MIXTURES OF 2,5-DIALKYL DIHYDROFURANONES AND 2,4,5-TRIALKYL DIHYDROFURANONES

This application is a continuation-in-part of Application for United States Letters Patent, Ser. No. 928,606 filed on July 27, 1978 now abandoned.

BACKGROUND OF THE INVENTION

This invention relates to novel 2,5-dialkyl dihydrofuranones and 2,4,5-trialkyl dihydrofuranones having the structures:

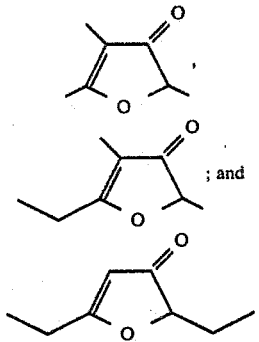

and mixtures of 2,5-dialkyl dihydrofuranones and 2,4,5-trialkyl dihydrofuranones having the structures:

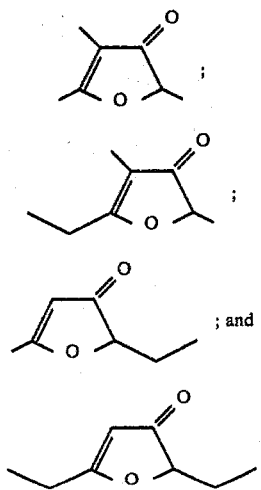

and the uses thereof in foodstuffs and foodstuff flavorings, chewing gums and toothpastes having sweet, brown sugar, pineapple-like, caramel, buttery, scorched butter-like, dried hazelnut and earthy aromas, and sweet, brown sugar-like, pineapple-like, caramel, buttery, cheese-like, roasted, vanilla-like, dried hazelnut and earthy tastes and has for an object the provision of a composition and process for improving the flavor and aroma of foodstuffs.

There has been considerable work performed relating to substances which can be used to impart (or enhance) flavors to (or in) various foodstuffs, chewing gums and toothpastes. These substances are used to diminish natural materials, some of which may be in short supply, and to provide more uniform properties in the finished product. Sweet, brown sugar, pineapple-like, caramel, buttery, scorched butter-like, dried hazelnut and earthy aromas, and sweet, brown sugar-like, pineapple-like, caramel, buttery, cheese-like, roasted, vanilla-like, dried hazelnut and earthy tastes are desirable for many uses in foodstuff flavors, chewing gum flavors and toothpaste flavors as well as foodstuffs per se, chewing gums per se and toothpastes per se, for example, maple, caramel, vanilla, butterscotch, rum, dairy, cereal, pineapple, roasted almond, and mushroom flavored foodstuffs.

German Offenlengungsschrift No. 2,359,891, published on June 6, 1974 entitled "2-alkyl-3(2H)-furanones" discloses the use of individual compounds having the generic structure:

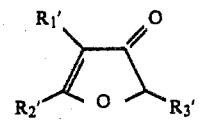

wherein $R_1'$ is hydrogen, hydroxyl, carboxyclic acid, or carboxylic acid ester and wherein $R_2'$ is $C_1$-$C_4$ alkyl and wherein $R_3'$ is hydrogen, or $C_1$-$C_7$ alkyl for use in foodstuffs and foodstuff flavors. The specific compound having the structure:

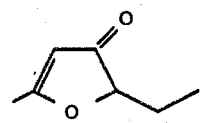

is also disclosed in said German Offenlengungsschrift No. 2,359,891. However, the compounds which are novel of our invention having the structures:

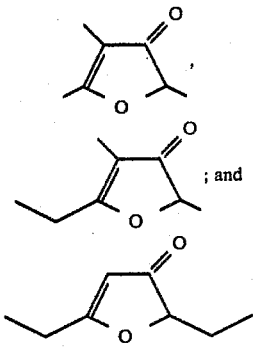

and the mixtures of our invention containing the compounds:

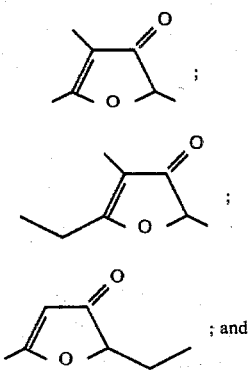

-continued

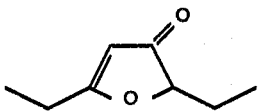

have aroma and flavor intensities and substantivities which are significantly greater than and improved over the compounds of Offenlengungsschrift No. 2,359,891; and are so unexpectedly advantageous in quality of aroma that these compounds and mixtures represent an advance in the art over the disclosure of German Offenlengungsschrift No. 2,359,891. Furthermore, the compounds of the instant case which are novel having the structures:

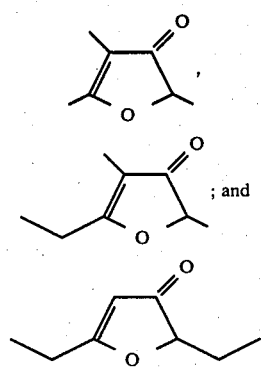

and the mixture of the four compounds having the structures:

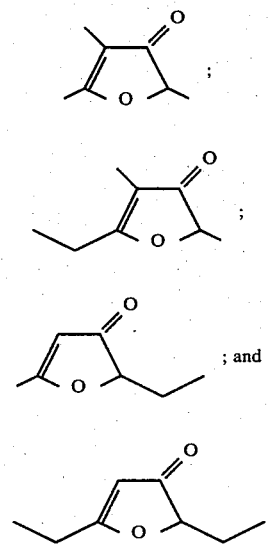

cannot be prepared by any process but that disclosed in the instant application. In addition, the processes set forth in Offenlengungsschrift No. 2,359,891 cannot be used to prepare the novel compounds of our invention or for that matter the mixtures of our invention.

The compounds of our invention and the mixtures of 2,5-dialkyl dihydrofuranones and 2,4,5-trialkyl dihydrofuranones of our invention, which 2,5-dialkyl dihydrofuranones and 2,4,5-trialkyl dihydrofuranones have the structures:

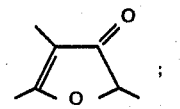

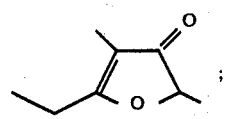

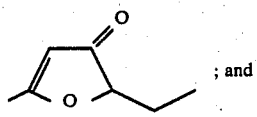

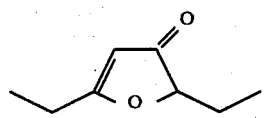

can be prepared according to a process as described in U.S. Pat. No. 3,980,675. However, said process described in U.S. Pat. No. 3,980,675 is limited to the production of 2,5-dimethyl-3-(2H) furanone having the structure:

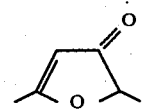

and there is no suggestion concerning a method which can be used to prepare the compounds useful in our invention or the mixtures of the four compounds of our invention. Thus, whereas the process of U.S. Pat. No. 3,980,675 is limited to dimerization of the compound diacetyl followed by hydrolysis in acid media according to the reaction sequence

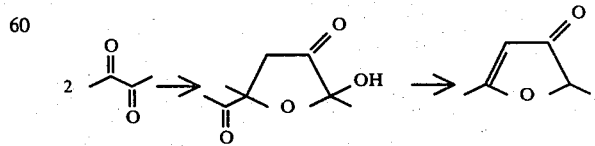

the process of our invention is embodied in the reaction sequence

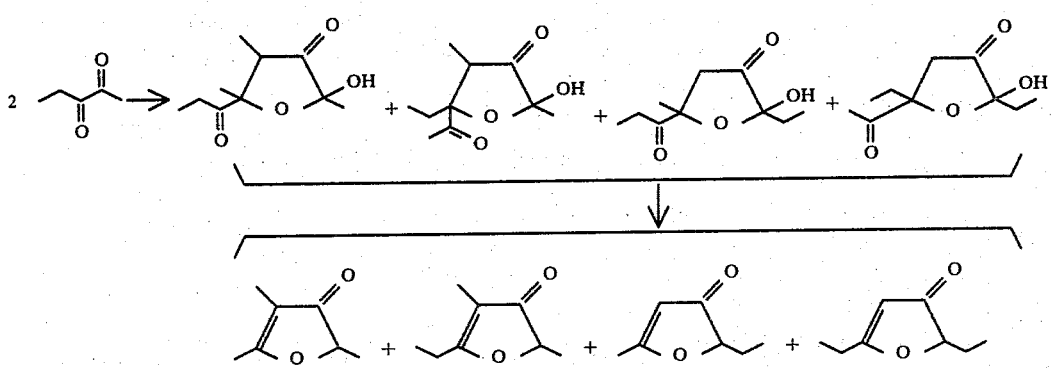

Accordingly, the process of our invention also represents an advance in the art over the process of U.S. Pat. No. 3,980,675.

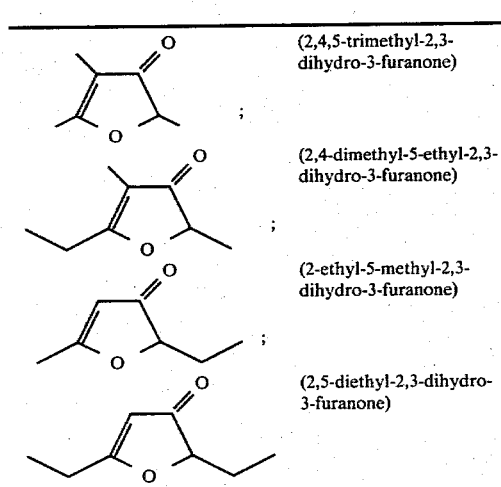

(2,4,5-trimethyl-2,3-dihydro-3-furanone);

(2,4-dimethyl-5-ethyl-2,3-dihydro-3-furanone);

(2-ethyl-5-methyl-2,3-dihydro-3-furanone);

(2,5-diethyl-2,3-dihydro-3-furanone)

produced according to Example I, and containing 37% compound having the structure:

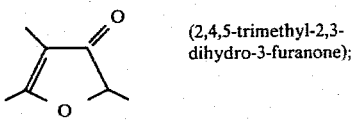

(2,4,5-trimethyl-2,3-dihydro-3-furanone);

15% of compound having the structure:

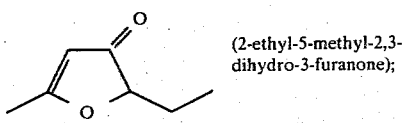

(2-ethyl-5-methyl-2,3-dihydro-3-furanone);

27% of compound having the structure:

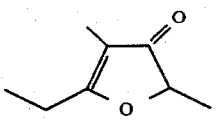

(2,4-dimethyl-5-ethyl-2,3-dihydro-3-furanone); and

15% of compound having the structure:

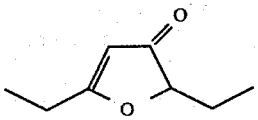

(2,5-diethyl-2,3-dihydro-3-furanone)

Figure 2:
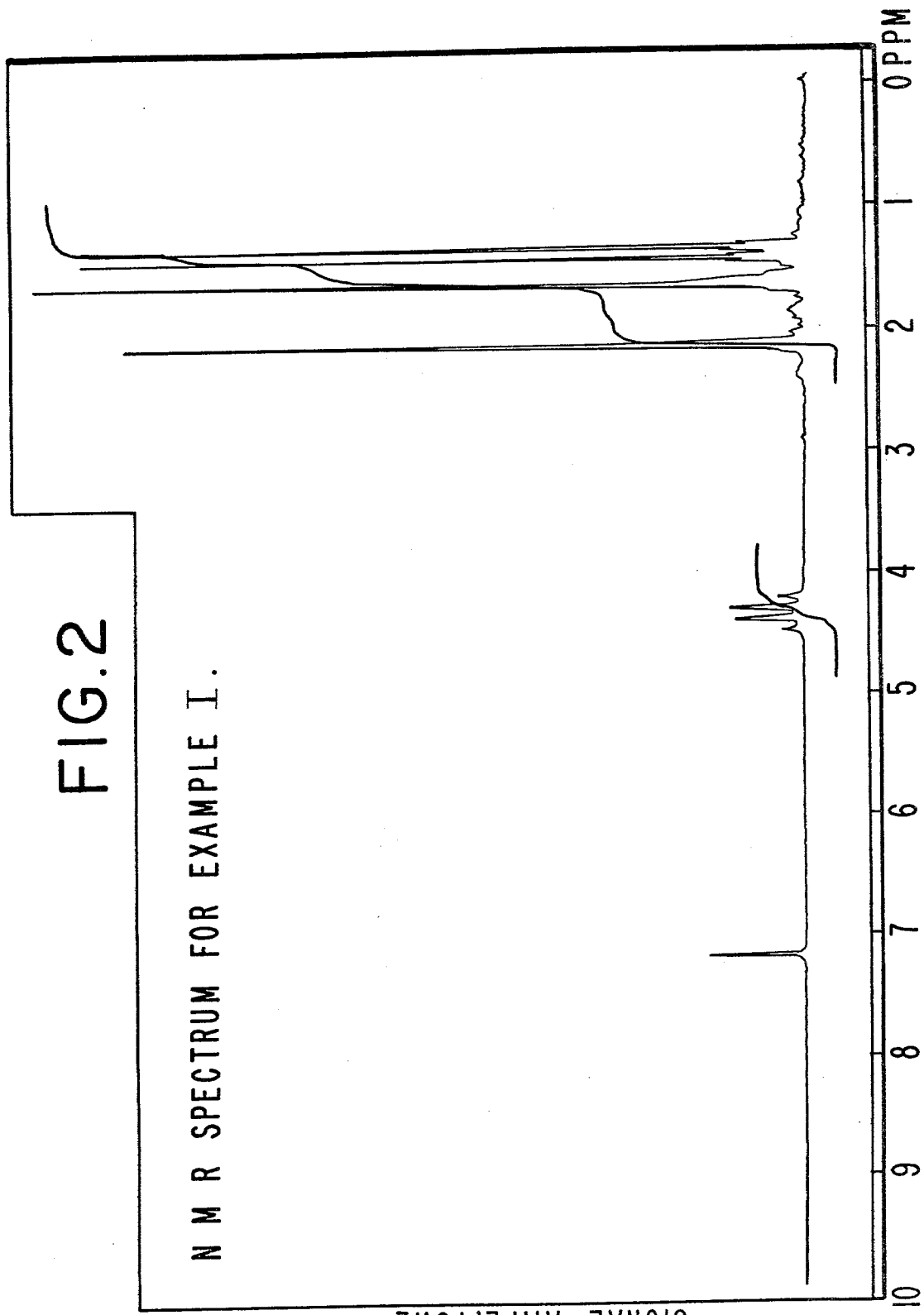

FIG. 2 is the NMR spectrum for the compound having the structure:

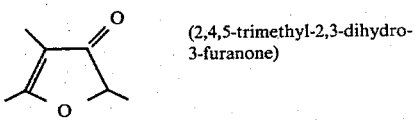

(2,4,5-trimethyl-2,3-dihydro-3-furanone)

produced according to Example I.

Figure 3:
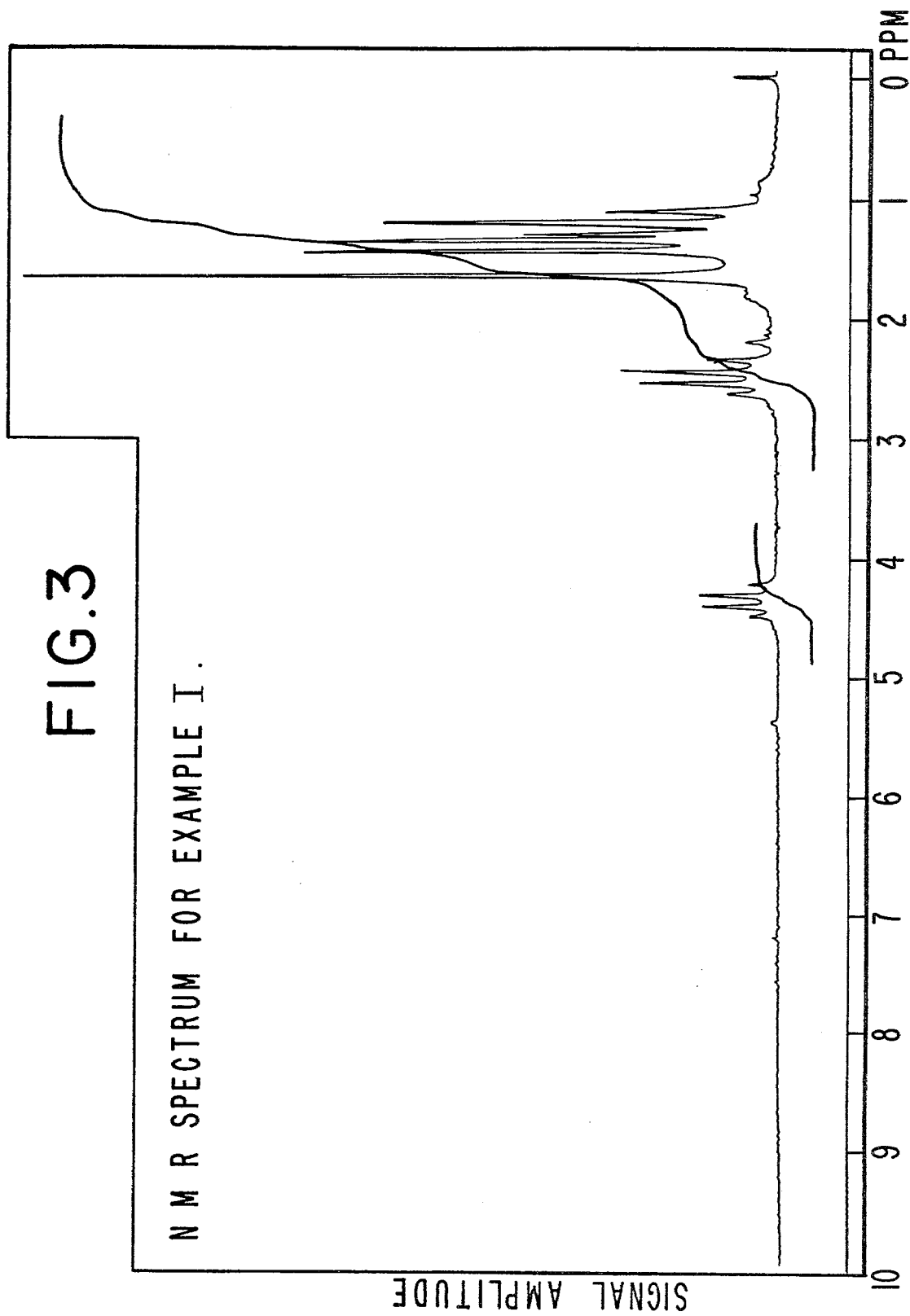

FIG. 3 is the NMR spectrum for the compound having the structure:

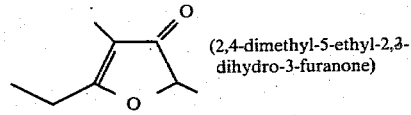

(2,4-dimethyl-5-ethyl-2,3-dihydro-3-furanone)

produced according to Example I.

Figure 4:
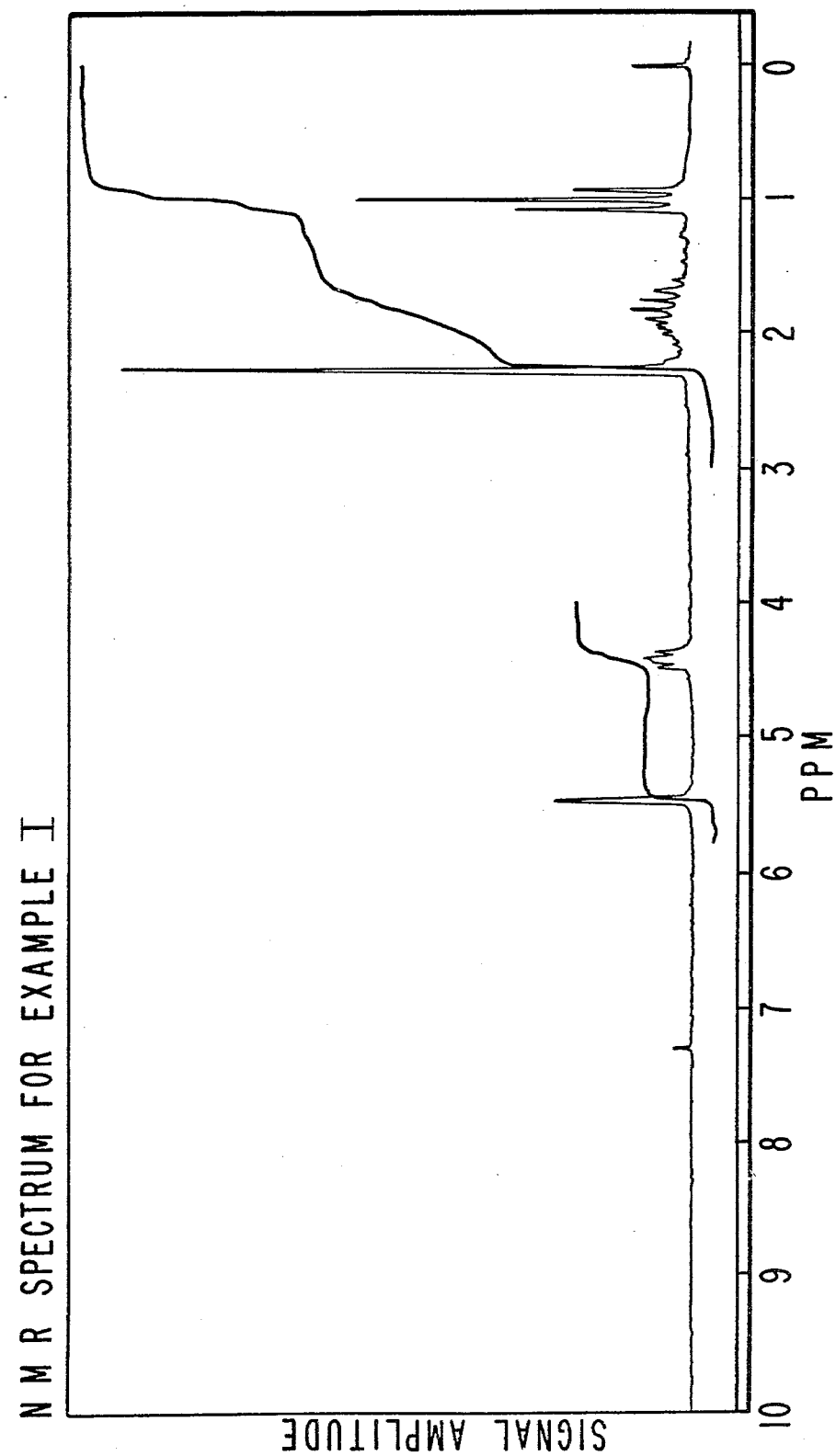

FIG. 4 is the NMR spectrum for the compound having the structure:

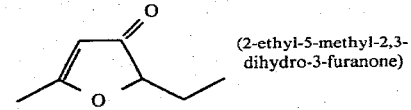

(2-ethyl-5-methyl-2,3-dihydro-3-furanone)

produced according to Example I.

Figure 5:
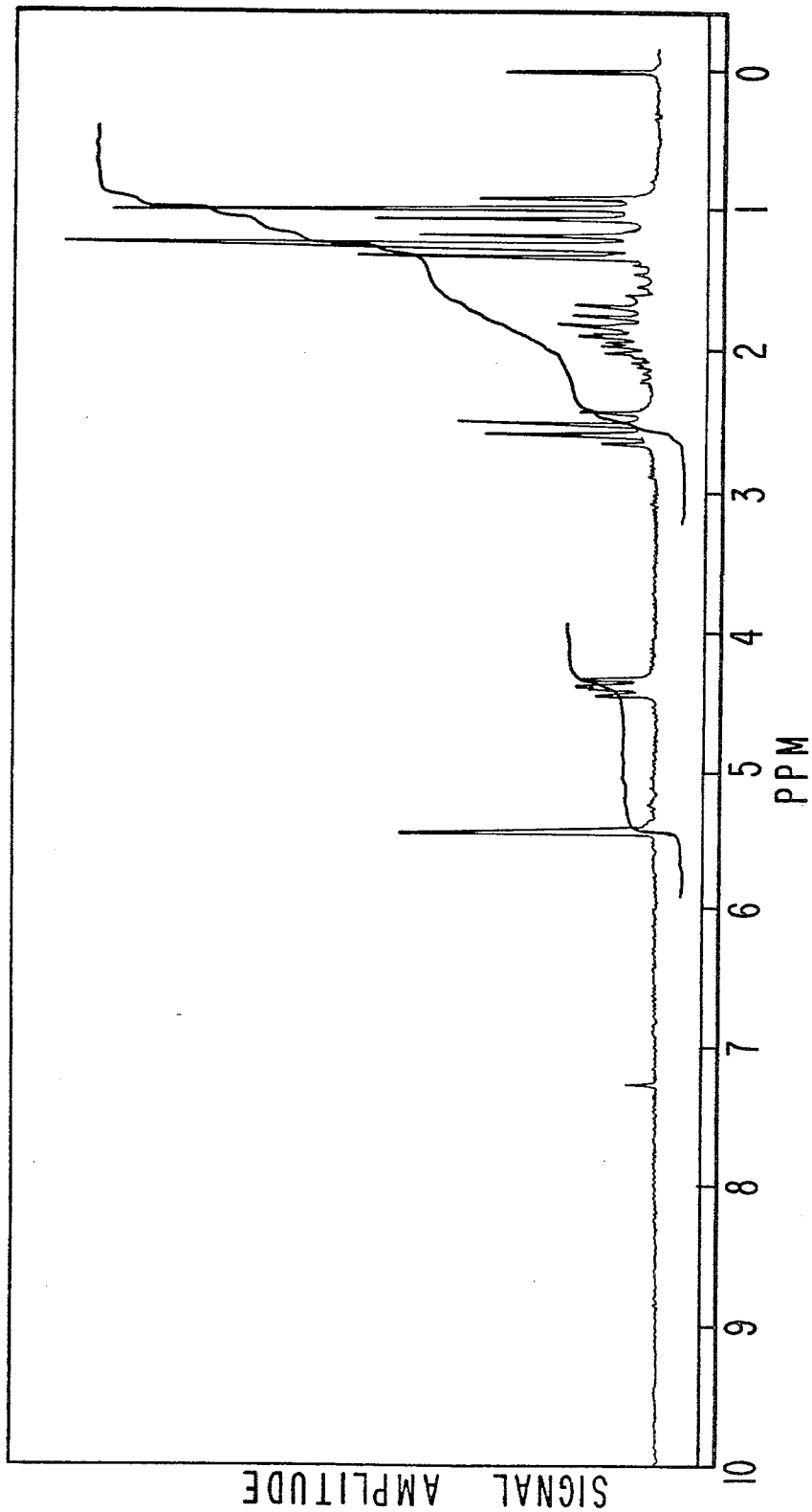

FIG. 5 is the NMR spectrum for the compound having the structure:

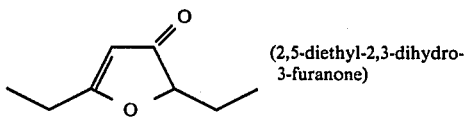 (2,5-diethyl-2,3-dihydro-3-furanone)

produced according to Example I.

Figure 6:
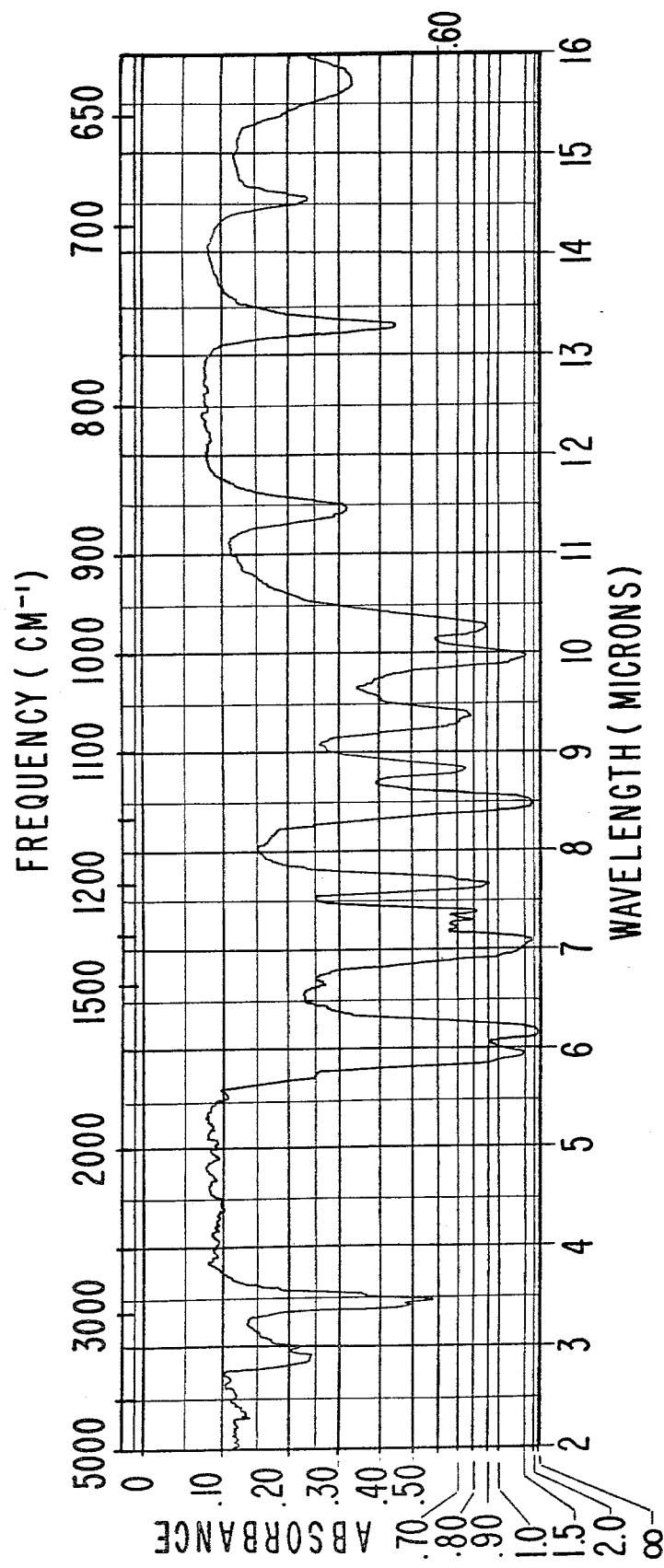

FIG. 6 is the infrared spectrum for the compound having the structure:

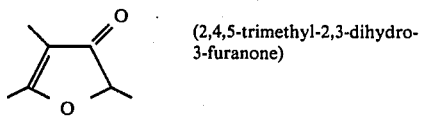 (2,4,5-trimethyl-2,3-dihydro-3-furanone)

produced according to Example I.

Figure 7:
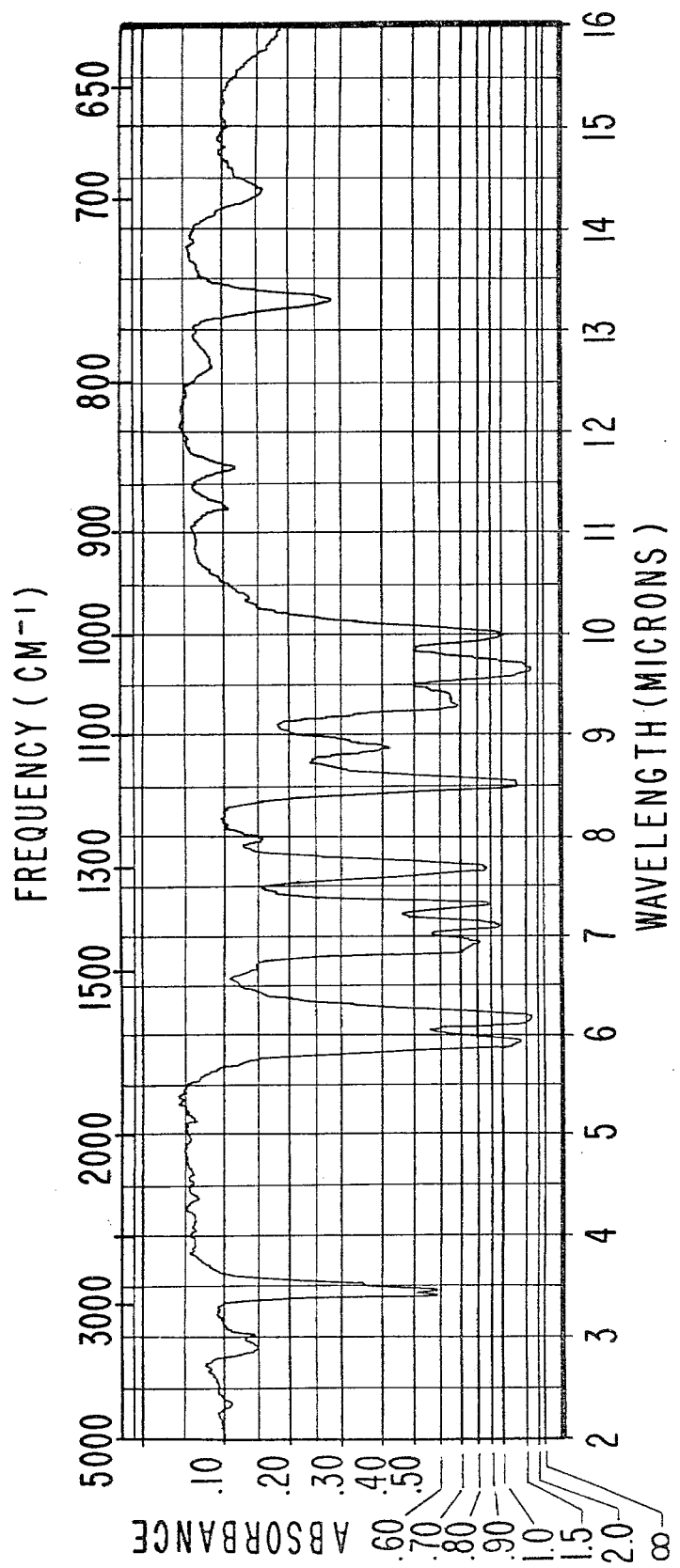

FIG. 7 is the infrared spectrum for the compound having the structure:

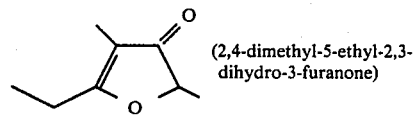 (2,4-dimethyl-5-ethyl-2,3-dihydro-3-furanone)

produced according to Example I.

Figure 8:
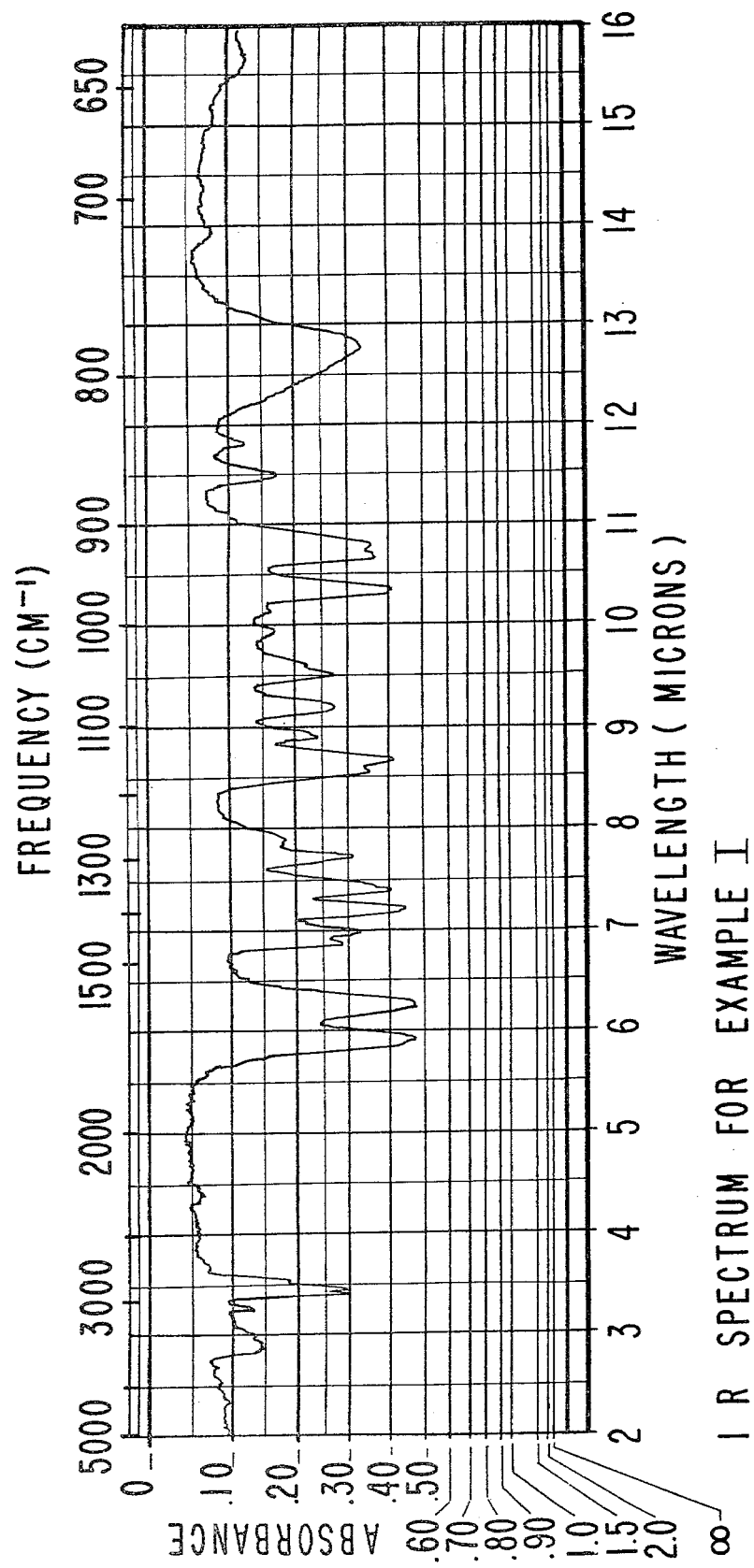

FIG. 8 is the infrared spectrum for the compound having the structure:

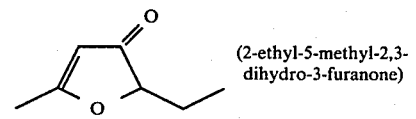 (2-ethyl-5-methyl-2,3-dihydro-3-furanone)

produced according to Example I.

Figure 9:
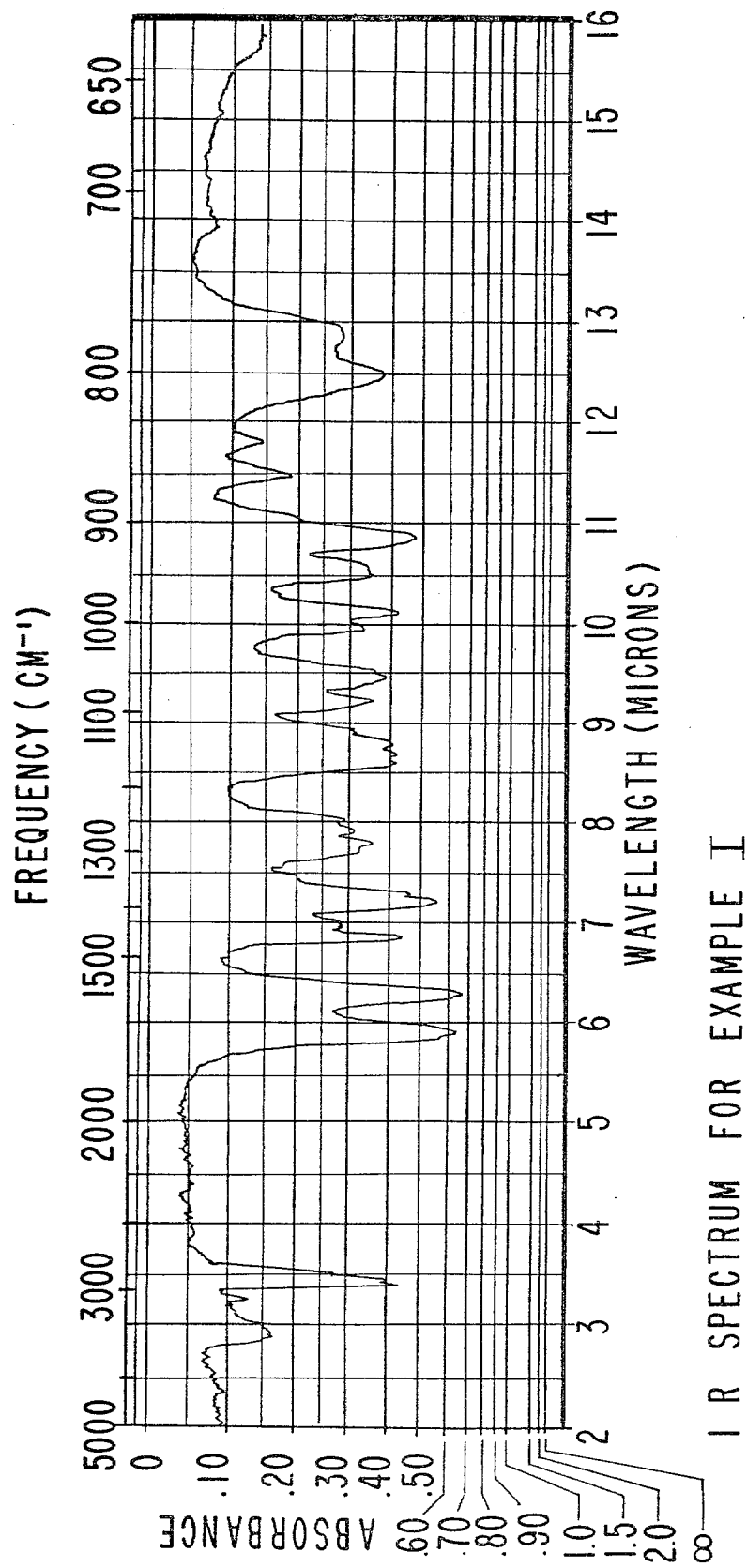

FIG. 9 is the infrared spectrum for the compound having the structure:

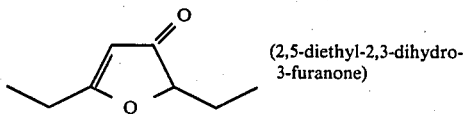 (2,5-diethyl-2,3-dihydro-3-furanone)

produced according to Example I.

Figure 10:
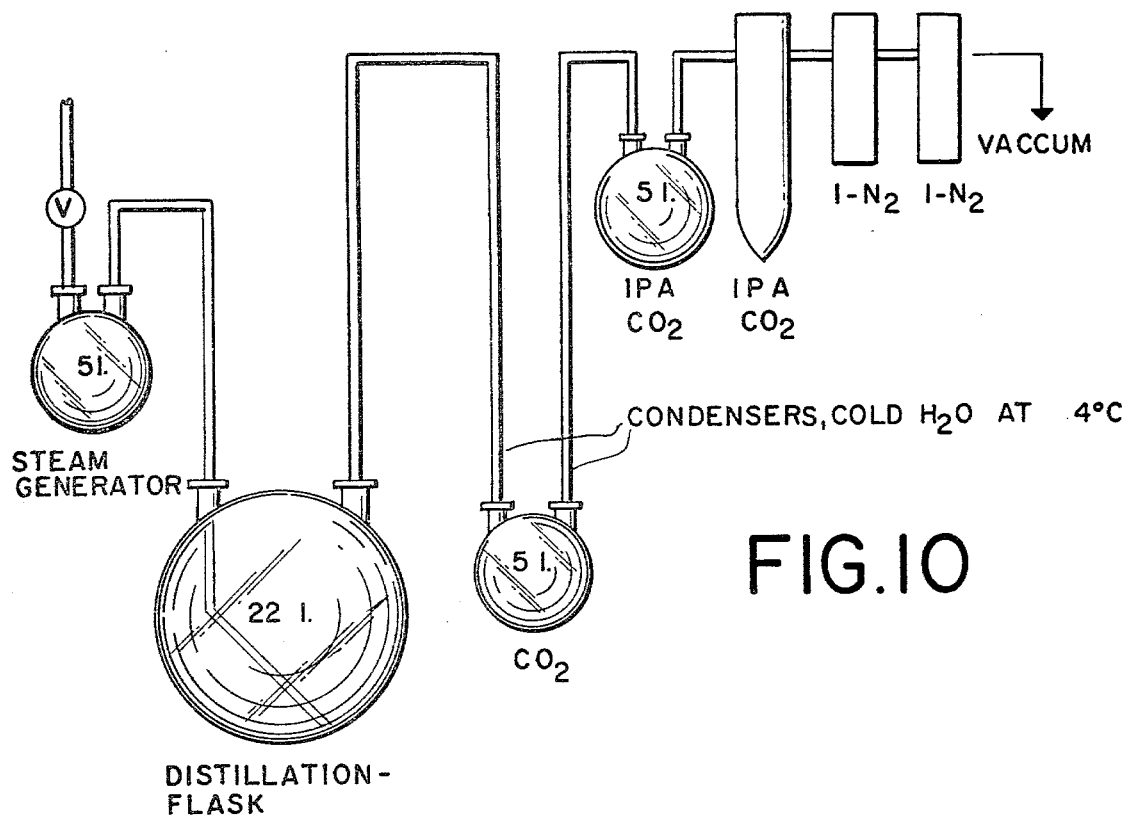

FIG. 10 sets forth the vacuum steam distillation apparatus used in the isolation of 2,4,5-trimethyl-3(2H)-furanone from bacon flavor of Example III.

Figure 11:
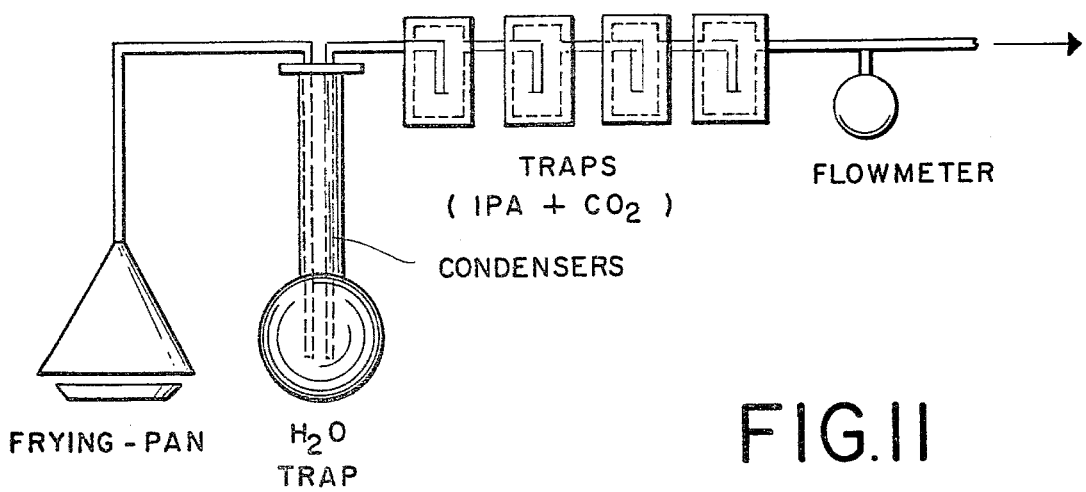

FIG. 11 is an illustration of the chemical separation scheme of Example III.

FIG. 12 is the GLC profile for the chromotographic fraction containing 2,4,5-trimethyl-3(2H)-furanone produced in Example III.

Figure 13:
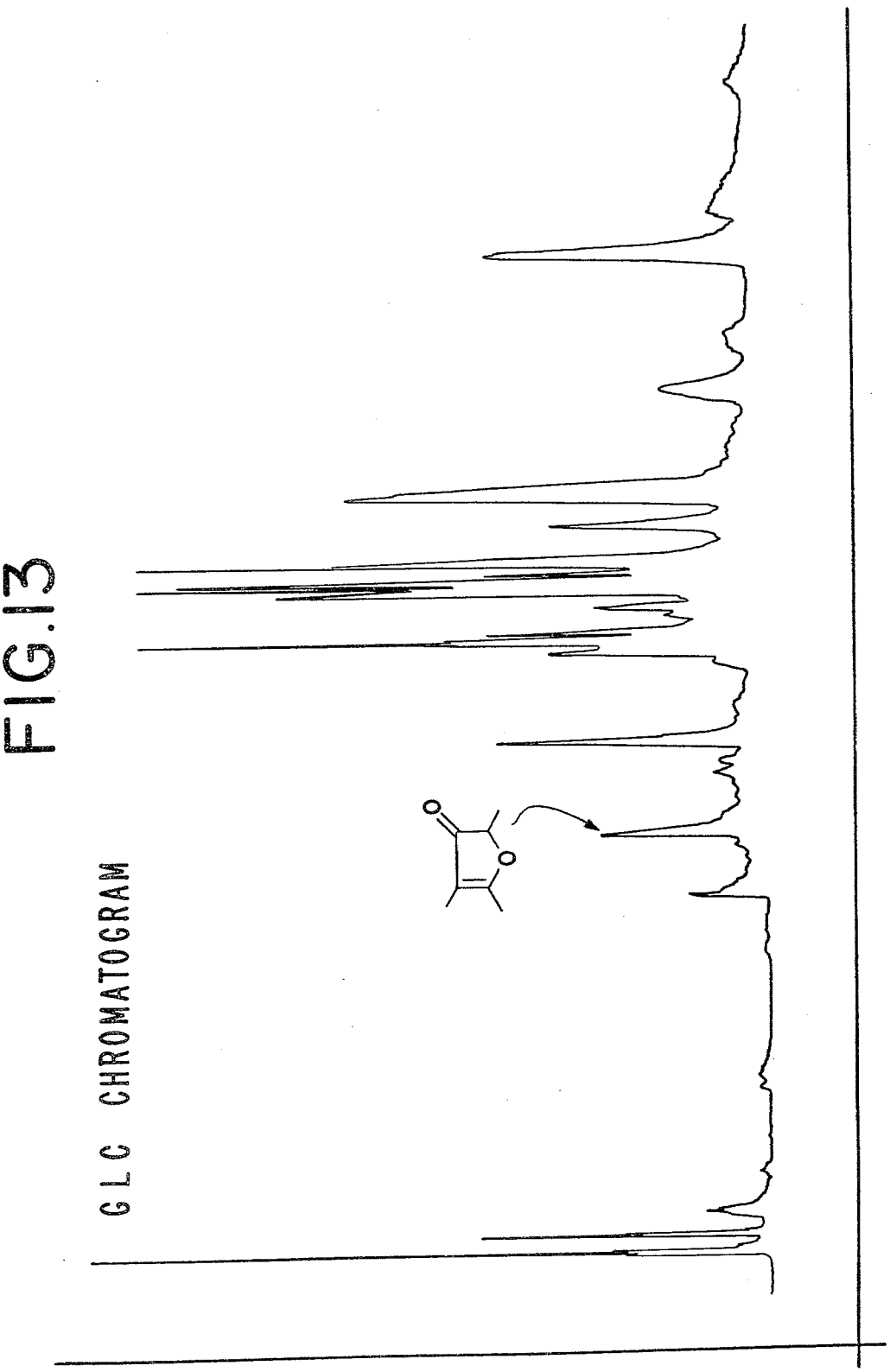

FIG. 13 is the GLC profile for 2,4,5-trimethyl-3(2H)-furanone produced according to Example III.

Figure 14:
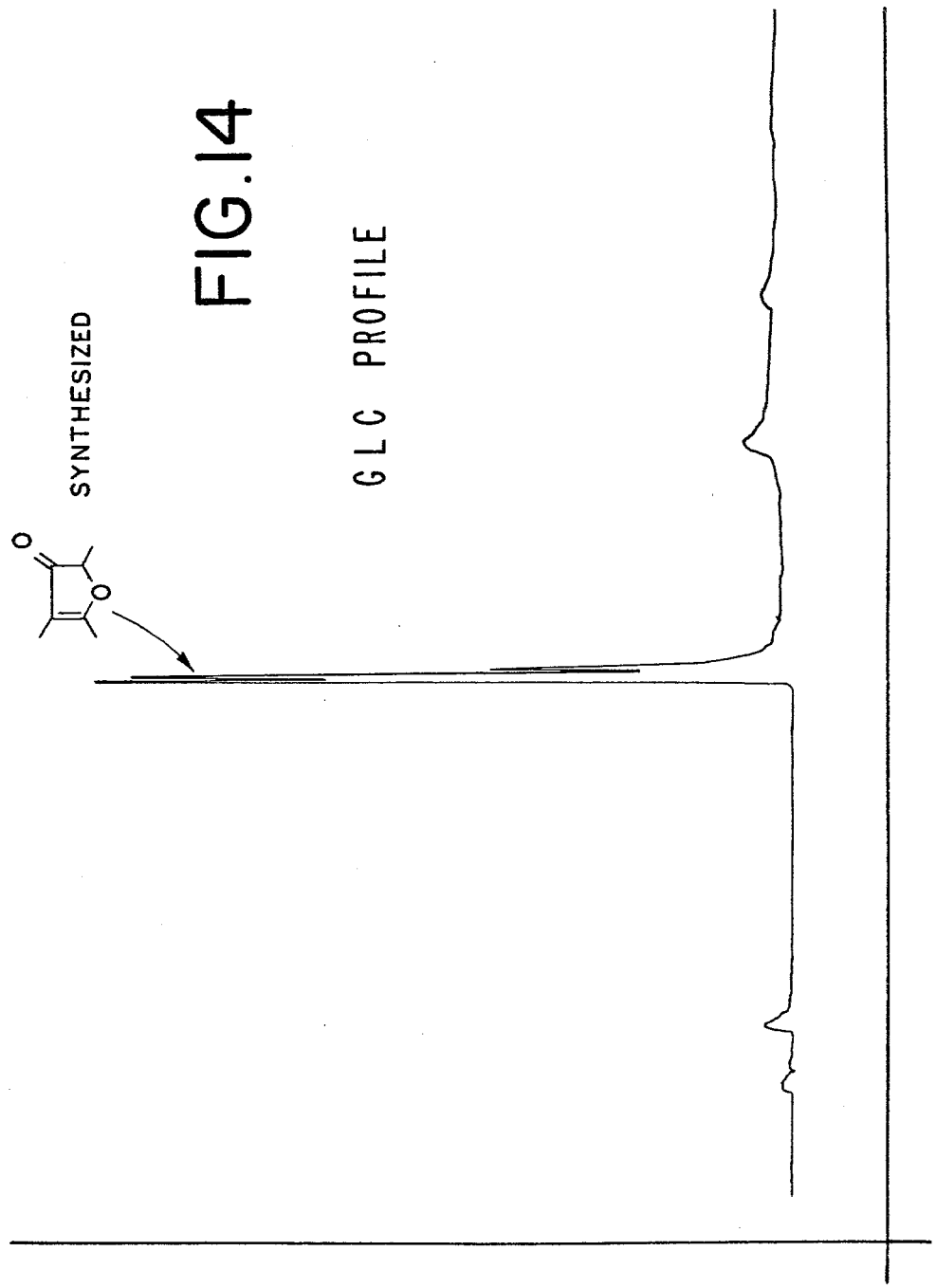

FIG. 14 is the infrared spectrum for the isolated 2,4,5-trimethyl-3(2H)-furanone of Example III.

Figure 15:
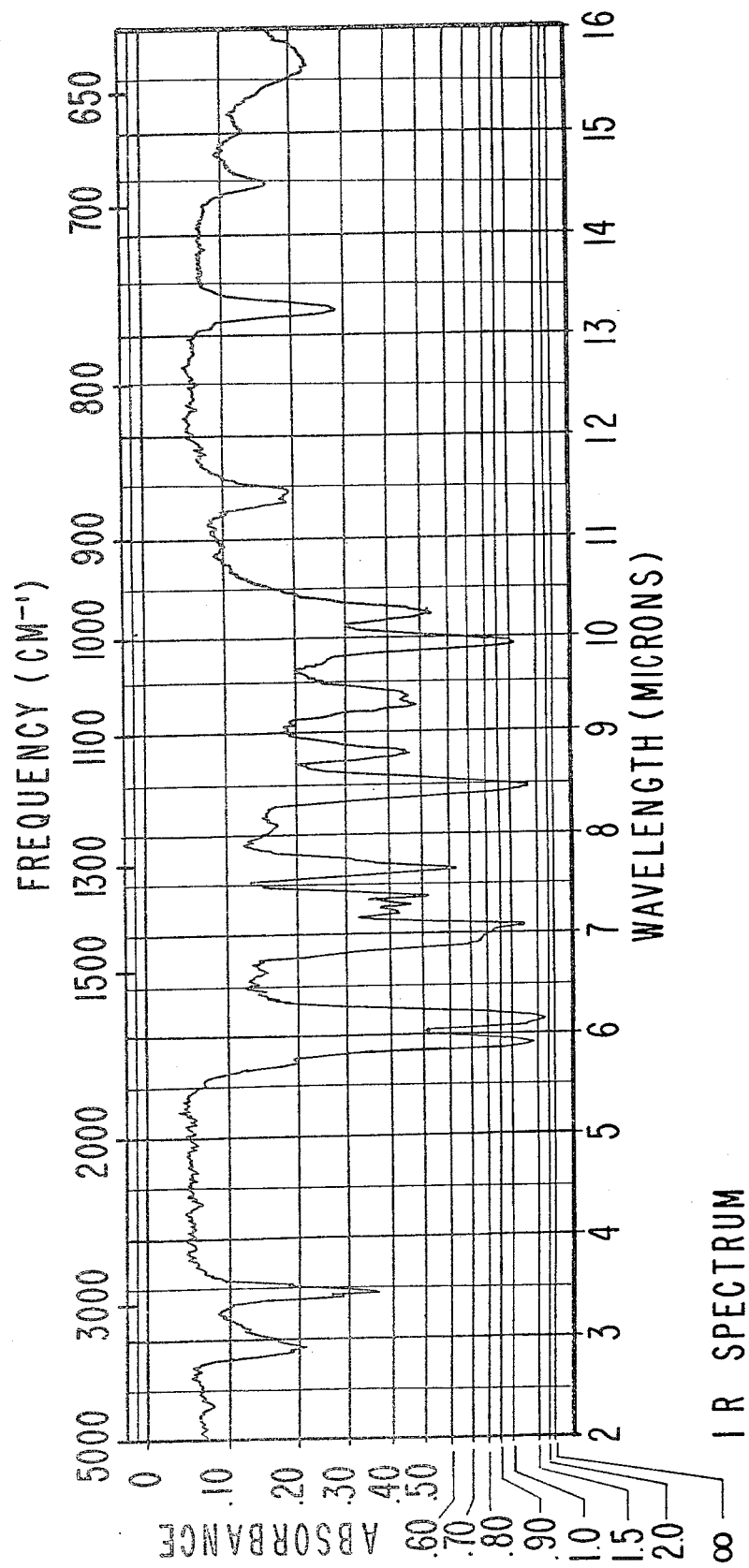

FIG. 15 is the NMR spectrum for the isolated 2,4,5-trimethyl-3(2H)-furanone produced in Example III.

Figure 16:
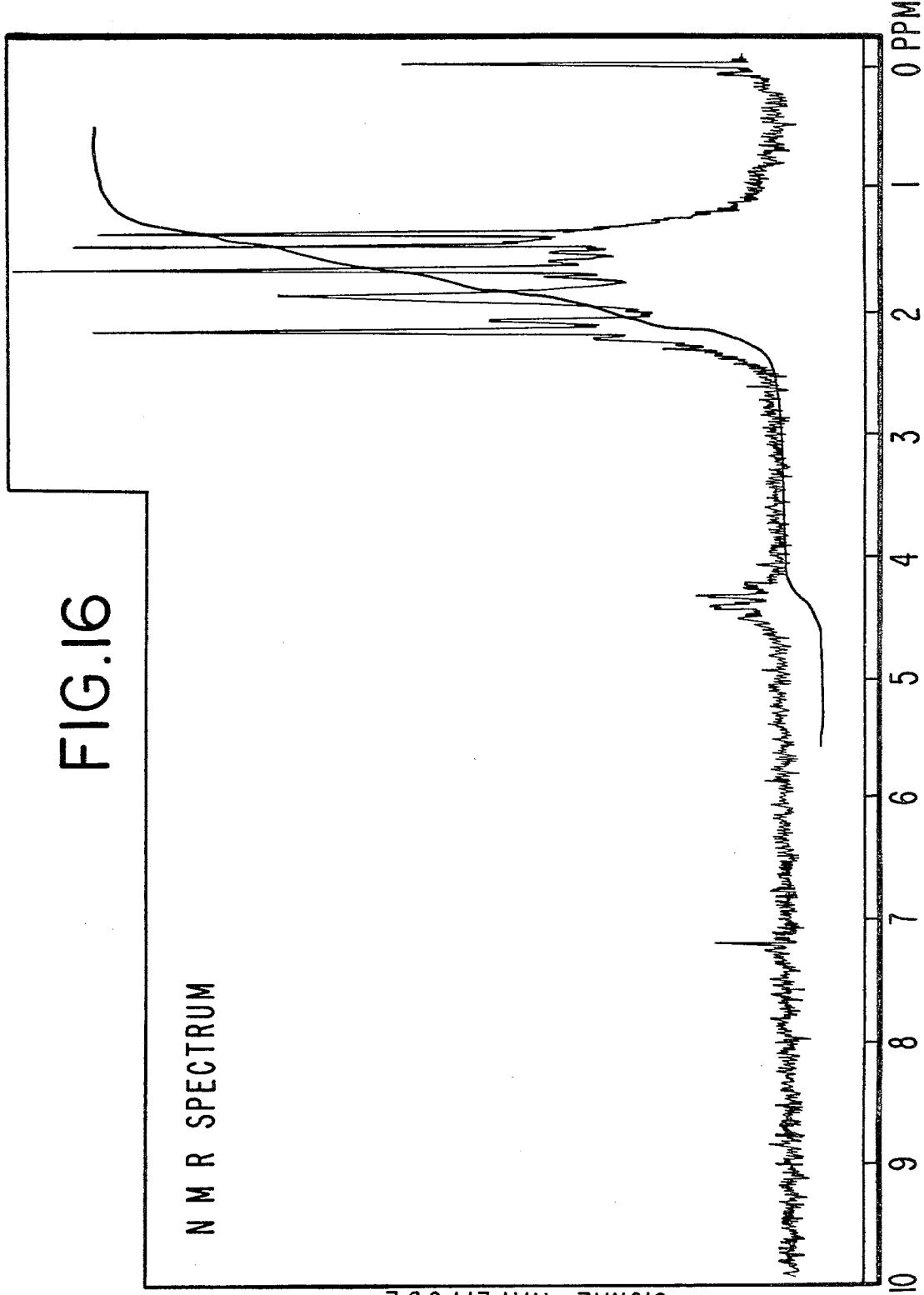

FIG. 16 is the mass spectrum for the isolated 2,4,5-trimethyl-3(2H)-furanone produced according to Example III.

THE INVENTION

The invention comprises novel compositions and foodstuffs containing dialkyl or trialkyl dihydrofuranones having the structures:

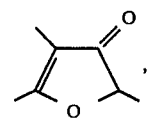 ,

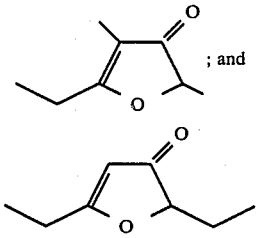 ; and or mixtures of the four compounds having the structures:

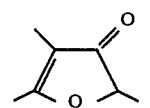 ;

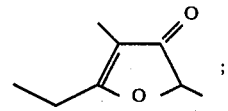 ;

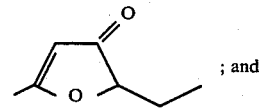 ; and

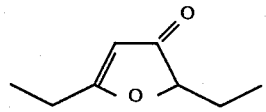

the specific embodiments of which are described hereinafter by way of example and in accordance with which it is now preferred to practice the invention.

Such dialkyl and trialkyl dihydrofuranones and mixtures are obtained by carrying out processes described in detail in U.S. Pat. No. 3,980,675 according to the following reaction scheme:

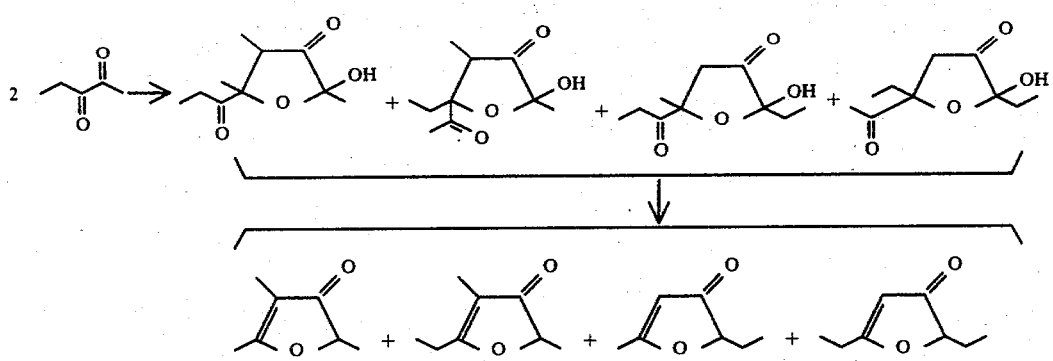

wherein 2,3-pentane-dione is first dimerized in the presence of an aldol condensation catalyst which can be a base such as potassium hydroxide, sodium hydroxide, barrium hydroxide, zinc hydroxide, sodium acetate, potassium acetate or zinc acetate at temperatures of between −10° C. and 50° C.; preferably at temperatures of between 0° C. and 10° C. The resulting dimers of 2,3-pentane-dione are four in number. These dimers are then hydrolyzed according to the procedure disclosed in detail in U.S. Pat. No. 3,980,675 at temperatures in the range of 0° C. up to 140° C. in the presence of mineral or organic acids or in the presence of cationic resins or water itself.

The speed of hydrolysis and the yield of the dialkyl and trialkyl dihydrofuranones are functions of several factors which are independent of each other insofar as the temperature, concentrations of acid used to catalyze the hydrolysis, type of acid used and duration of the reaction are concerned. Variations in the concentration of the starting dimerization product however do not appear to significantly effect the yield of mixture of compounds having the structures:

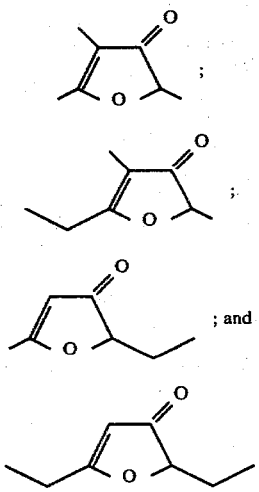

at least within the range of parameters for converting the dimer mixture to the dihydro furanone reaction product mixture in accordance with the preferred embodiments of our process and which are as follows:
 (a) temperature: between 20° C. and 120° C.
 (b) concentration of dimerization products (in grams/100 cc of solution): between 3 and 11 based on 100% conversion of the 2,3-pentane-dione in the aldol condensation reaction;
 (c) acid concentration: (in grams/100 cc of solution) between 0.04 and 4.0;
 (d) duration of reaction: between 1 and 8 hours.

Acids which are particularly suitable for use in the process because of both effectiveness and ready availability are:
 (i) hydrochloric acid, preferably concentrated;
 (ii) sulfuric acid between 40 and 60% concentration (weight percent);
 (iii) formic acid;
 (iv) glacial acidic acid; and
 (v) cation exchange resins.

The hydrolysis product can readily be extracted from the aqueous solution in which it is formed and which optionally may be saturated with a mineral salt such as, for example, sodium chloride or potassium chloride, by means of solvents such as diethyl ether, chloroform, 1,2-dichloro ethane or tetrahydro furane by conventional extracting techniques.

After the extracting agent is removed by flash distillation, the resulting crude material may be fractionally distilled in vacuum to yield a number of fractions each of which fraction contains varying quantities of the compounds having the structures:

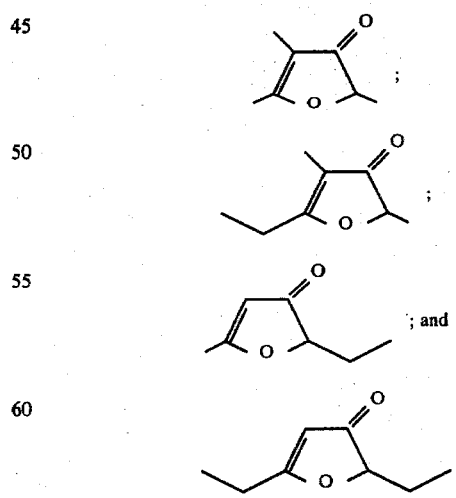

as more particularly described in the following examples.

The resulting mixtures may also be separated by means of various chromatographic techniques such as gas chromotography, or liquid chromotography or high-pressure liquid chromotography whereby the following compounds having the following properties may be obtained:

| Compound Structure | Name | Flavor property |
|---|---|---|
| (structure) | 2,4,5-trimethyl-2,3-dihydro-3-furanone | A sweet, carmel, buttery and scorched butter aroma character with a sweet, caramel, buttery, cheesey roasted and vanilla flavor characteristic at 5ppm in water. |
| (structure) | 2,4-dimethyl-5-ethyl-2,3-dihydro-3-furanone | A dried hazelnut, earthy, caramel-like and buttery aroma with a dried hazelnut, earthy, caramel-like and buttery flavor at 5ppm in water. |
| (structure) | 2-ethyl-5-methyl-2,3-dihydro-3-furanone | A buttery, brown sugar-like, pineapple-like caramel-like aroma and flavor characteristic at 10ppm in water. |
| (structure) | 2,5-diethyl-2,3-dihydro-3-furanone | A brown sugar-like, caramel and buttery aroma and flavor characteristic at 25ppm. |

One aspect of our invention resides in its commercial importance as illustrated by the fact that it is not necessary to separate out the several di and tri substituted dihydrofuranones produced according to our invention but to leave the resulting distilled mixtures in that state whereby these mixtures may be used for their specific flavor nuances in caramel, butterscotch, rum, dairy, vanilla and roasted almond flavored foodstuffs and confections.

These mixtures contain the following ranges of proportions of ingredients:

| Compound Structure | Name | Weight Percent |
|---|---|---|
| (structure) | 2,4,5-Trimethyl-2,3-dihydro-3-furanone | 10-40 |
| (structure) | 2,4-dimethyl-5-ethyl-2,3-dihydro-3-furanone | 10-30 |
| (structure) | 2-ethyl-5-methyl-2,3-dihydro-3-furanone | 5-20 |
| (structure) | 2,5-diethyl-2,3-dihydro-3-furanone | 5-20 |

When the dialkyl or trialkyl dihydrofuranone or mixtures of dialkyl and trialkyl dihydrofuranones of our invention are used as food flavor adjuvants or are used to augment or enhance the flavor aroma characteristics of foodstuffs, the nature of the coingredients included with said 2,5-dialkyl dihydrofuranones and/or 2,4,5-trialkyl dihydrofuranones in formulating the product composition will also serve to augment the organleptic characteristics of the ultimate foodstuff treated therewith.

As used herein in regard to flavors, the term "augment" in its various forms means "supplying or imparting flavor character or note to otherwise bland, relatively tasteless substances, or augmenting the existing flavor characteristic where a natural flavor is deficient in some regard, or supplementing the existing flavor impression to modify its quality, character or taste."

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solids and liquids, and ingestible materials or chewable but non-ingestible materials such as chewing gum or chewable medicinal tablets. Such materials usually do, but need not, have nutritional value. Thus, foodstuffs include soups, convenience foods, beverages, gelatin desserts, dairy products, candies, vegetables, cereals, soft drinks, snacks, medicinal products such as cough mixtures and cough drops and the like.

Substances suitable for use herein as co-ingredients or flavoring adjuvants are well known in the art for such use, being extensively described in relevant literature. Apart from the requirements that any such materials be organoleptically compatible with the dialkyl and trialkyl substituted dihydrofuranones and mixtures thereof of our invention, non-reactive with the dialkyl and trialkyl dihydrofuranones and mixtures thereof of our invention and "ingestibly" acceptable and thus non-toxic or otherwise non-deleterious, nothing particularly critical resides in the selection thereof. Accordingly, such materials which in general may be characterized as flavoring adjuvants or vehicles comprise broadly stabilizers, thickeners, surface active agents, conditioners, other flavorants and flavor intensifiers.

Stabilizer compounds include preservatives, e.g. sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chloride, sodium hypochloride, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric, curcumin and the like; firming agents such as aluminum sodium sulfate, calcium chloride and calcium gluconate; texturizers, anti-caking agents, e.g., aluminum calcium sulfate and tribasic calcium phosphate; enzymes, e.g. mylase; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., fatty saturated acids, unsaturated acids, and amino acids; alcohols, e.g., primary and secondary alcohols; esters, carbonyl compounds including aldehydes and ketones as well as lactones; cyclic organic materials including benzene derivatives; isocyclics; heterocyclics such as furans, particularly 2,5-dimethyl-3-acetal furan and 2-methyl-2,3-dihydrofuran-3-one, pyridines, pyrazines (particularly monoalkyl, dialkyl, trialkyl and tetraalkyl substituted pyrazines) and the like, sulfur-containing materials including thiazoles, disulfides, thiols, sulfides, aldehydes, (for example, 3-phenyl-4-pentenal, 3-phenyl-3-pentenal, 3-phenyl-2-pentenal, 2-phenyl-2-pentenal and 2-phenyl-3-methyl-2-butenal); disulfides and the like; other flavor potentiators such as monosodium glutamate; guanylates, inosinates, natural and synthetic flavorants such as vanillin, ethyl vanillin, diacetyl, phenethyl-2-furoate, maltol, ethyl maltol, natural gums and the like; spices, herbs, essential oils and extractives including "bitterness principles" such as theobromin, caffein, naringin and other suitable materials creating a bitter effect.

The specific flavoring adjuvant selected for use may be either solid or liquid depending upon the desired physical form of the ultimate product, i.e., foodstuff, whether simulated or natural, and should, in any event, be capable of providing an environment in which the 2,5-dialkyl dihydrofuranones and/or 2,4,5-trialkyl dihydrofuranones can be dispersed or admixed to provide a homogeneous medium. In addition, selection of one or more flavoring adjuvants as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of 2,5-dialkyl dihydrofuranones and/or 2,4,5-trialkyl dihydrofuranones employed in a particular instance can vary over a relatively wide range whereby to its desired organoleptic effects having reference to the nature of the product are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of 2,5-dialkyl dihydrofuranones and/or 2,4,5-trialkyl dihydrofuranones will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of 2,5-dialkyl dihydrofuranones and/or 2,4,5-trialkyl dihydrofuranones ranging from a small but effective amount, e.g., 0.1 part per million up to about 50 parts per million by weight based on total composition are suitable when used alone without other cyclic di-ketones. Further, when used with such cyclic di-ketones as maltol, cyclotene, and 2,5-dimethyl-4-hydroxy-3(2H)-furanone, the concentration of 2,5-dialkyl dihydrofuranones and/or 2,4,5-trialkyl dihydrofuranones can be as low as 0.05 part per million. Concentrations in excess of the maximum quantities stated are not normally recommended since they fail to provide commensurate enhancement or organoleptic properties. In those instances wherein the 2,5-dialkyl dihydrofuranones and/or 2,4,5-trialkyl dihydrofuranones is added to the foodstuff as an integral component of a flavoring composition, it is, of course, essential that the total quantity of flavoring composition employed be sufficient to yield an effective 2,5-dialkyl dihydrofuranone and/or 2,4,5-trialkyl dihydrofuranone concentration in the foodstuff product.

Food flavoring compositions prepared in accordance with the present invention preferably contain the 2,5-dialkyl dihydrofuranones and/or trialkyl dihydrofuranones in concentrations ranging from about 0.1% up to about 10% by weight based on the total weight of said flavoring composition when the 2,5-dialkyl dihydrofuranone and/or 2,4,5-trialkyl dihydrofuranone is used without other cyclic di-ketones.

The compositions described herein can be prepared according to conventional techniques well known as typified by cake batters, and "fruit" juices can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the 2,5-dialkyl dihydrofuranones and/or 2,4,5-trialkyl dihydrofuranones with, for example, gum arabic, gum tragacanth, carrageenan and the like, and thereafter, spray drying the resultant mixture whereby to obtain the particular solid product. Pre-prepared flavor mixes in powder form, e.g. a vanilla powder or "maple sugar" flavored powder obtained by mixing the dried solid components, e.g., starch, sugar and the like and 2,5-dialkyl dihydrofuranones and/or 2,4,5-trialkyl dihydrofuranones, in a dry blender until the requisite degree of uniformity is achieved.

It is presently preferred to combine with the 2,5-dialkyl dihydrofuranones and/or 2,4,5-trialkyl dihydrofuranones the following adjuvants.

Eugenol
Guaiacol
Vanillin
Sucrose
Heliotropin
Ethyl Vanillin
Maltol
Ethyl Maltol
Cyclotene
Ethyl Cyclotene
Methyl Cyclopentenolone Butyrate
2,5-Dimethyl-4-Hydroxy-3(2H)-Furanone
Isovaleraldehyde
5-methyl furfural
Rum Ether
Pyruvic acid and
Ethyl butyrate The following examples are given to illustrate embodiments of the invention as it is presently preferred to practice it. It will be understood that these examples are illustrative and that the invention is not to be considered as restricted thereto except as indicated in the appended claims.

EXAMPLE I

PREPARATION OF MIXTURE OF
2,4,5-TRIMETHYL-2,3-DIHYDRO-3-FURANONE;
2,4-DIMETHYL-5-ETHYL-2,3-DIHYDRO-3-FURANONE;
2-ETHYL-5-METHYL-2,3-DIHYDRO-3-FURANONE; AND
2,5-DIETHYL-2,3-DIHYDRO-3-FURANONE

Reaction

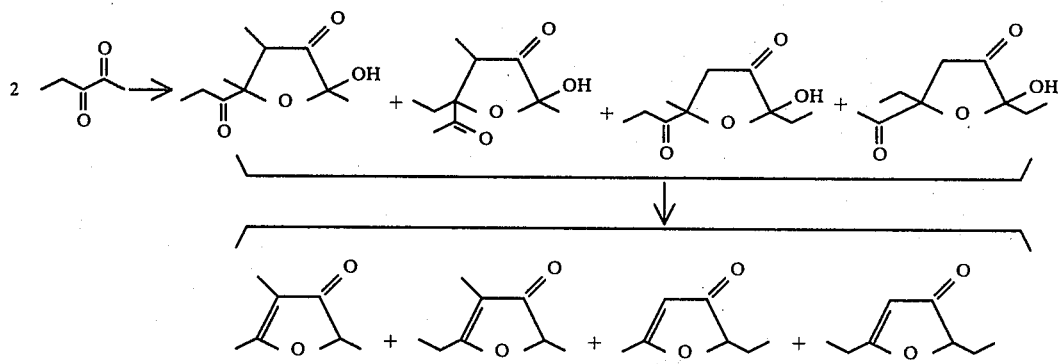

Part A. Preparation of compounds:

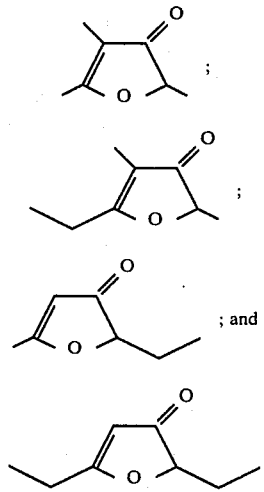

Into a 2 liter reaction flask equipped with mechanical stirrer, condenser, addition funnel and thermometer is placed 2.5 moles (250 grams) of 2,3 pentane dione. Over a period of 1.5 hours at a temperature range of from −2° C. up to +6° C., 350 ml of 20% KOH solution (acqueous) is added to the reaction mass with stirring. The reaction mass pH is then adjusted to 7 using 50% hydrochloric acid. 40 ml concentrated hydrochloric acid is then added to the reaction mass which is then heated using steam to 95° C. and maintained at 95° C. over a period of 6.5 hours. The pH of the reaction mass is then adjusted to 7 using a 25% acqueous solution of sodium hydroxide. The reaction mass is saturated with sodium chloride then extracted with one portion of 500 ml anhydrous diethyl ether and two portions of 250 ml each of anhydrous diethyl ether. The diethyl ether extracts are combined and washed to two 75 ml portions of saturated sodium bicarbonate followed by three 150 ml portions of saturated sodium chloride. The resulting extract is then concentrated yielding 262 grams of crude containing 55% solvent. The crude is then rush over-distilled in a 500 ml distillation flask into 12 fractions. Half of the fractions 3–8 are combined and distilled on a spinning band column yielding 22 fractions. The fractional distillation data is as follows:

| No. | Vapor Temp. (°C.) | Liquid Temp (°C.) | Vac. mm. Hg | Wt. of Fraction g. |
|---|---|---|---|---|
| 1 | 23–75 | 40–104 | 40–38 | 10.2 |
| 2 | 87 | 120 | 38 | 14.5 |
| 3 | 96 | 130 | 38 | 11.1 |
| 4 | 98 | 135 | 38 | 11.0 |
| 5 | 101 | 144 | 38 | 11.4 |
| 6 | 103 | 151 | 38 | 8.6 |
| 7 | 108 | 159 | 38 | 10.9 |
| 8 | 114 | 164 | 37 | 9.3 |
| 9 | 130 | 166 | 28 | 14.6 |
| 10 | 128 | 172 | 18 | 17.6 |
| 11 | 160 | 190 | 18 | 19.4 |
| 12 | 160 | 198 | 16 | 24.6 |

The spinning band distillation data is as follows:

| No. | Vapor Temp. (°C.) | Liquid Temp. (°C.) | Vac. mm. Hg | Reflux Ratio |
|---|---|---|---|---|
| 1 | 26 | 55–98 | 65 | 1:1 |
| 2 | 56 | 105 | 32 | 1:1 |
| 3 | 59 | 104 | 32 | 1:1 |
| 4 | 59 | 106 | 32 | 1:10 |
| 5 | 59 | 106 | 32 | 1:10 |
| 6 | 59 | 108 | 32 | 1:15 |
| 7 | 59 | 109 | 32 | 1:15 |
| 8 | 62 | 110 | 32 | 1:15 |
| 9 | 74 | 111 | 32 | 1:15 |
| 10 | 76 | 114 | 32 | 1:15 |
| 11 | 76 | 116 | 32 | 1:15 |
| 12 | 80 | 116 | 32 | 1:15 |
| 13 | 80 | 118 | 32 | 1:15 |
| 14 | 80 | 121 | 32 | 1:15 |
| 15 | 84 | 122 | 30 | 1:15 |
| 16 | 93 | 126 | 30 | 1:15 |
| 17 | 95 | 127 | 30 | 1:15 |
| 18 | 86 | 146 | 32 | 1:15 |
| 19 | 78 | 152 | 24 | 1:15 |
| 20 | 76 | 142 | 10 | 1:15 |
| 21 | 76 | 172 | 8 | 1:15 |
| 22 | 38 | 176 | 1 | 1:15 |

Fractions 3–8 from the rushover distillation yield contain the following compounds:

29% of compound having the structure:

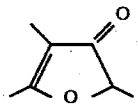

12% of compound having the structure:

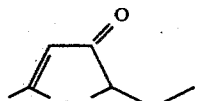

17% of compound having the structure:

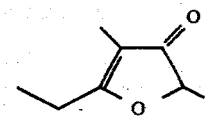

12% of compound having the structure:

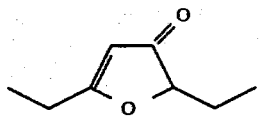

This mixture is hereinafter referred to as mixture "A".

The spinning band distillation yields the following:

Fraction 7: 98% pure compound having the structure:

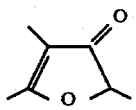

Fraction 10: 90% pure compound having the structure:

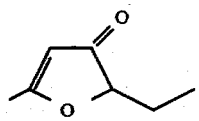

Fraction 15: 96% pure compound having the structure:

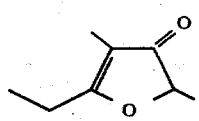

Fraction 19: 94% pure compound having the structure:

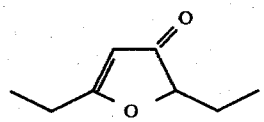

FIG. 2 is the NMR spectrum for 2,4,5-trimethyl-2,3-dihydro-3-furanone produced according to Example I.

FIG. 3 is the NMR spectrum for 2,4-dimethyl-5-ethyl-2,3-dihydro-3-furanone produced according to Example I.

FIG. 4 is the NMR spectrum for 2-ethyl-5-methyl-2,3-dihydro-3-furanone produced according to Example I.

FIG. 5 is the NMR spectrum for 2,5-diethyl-2,3-dihydro-3-furanone produced according to Example I.

FIG. 6 is the infrared spectrum for 2,4,5-trimethyl-2,3-dihydro-3-furanone produced according to Example I.

FIG. 7 is the infrared spectrum for 2,4-dimethyl-5-ethyl-2,3-dihydro-3-furanone produced according to Example I.

FIG. 8 is the infrared spectrum for 2-ethyl-5-methyl-2,3-dihydro-3-furanone produced according to Example I.

FIG. 9 is the infrared spectrum for 2,5-diethyl-2,3-dihydro-3-furanone produced according to Example I.

Part B: Commercial preparation of mixture of compounds having the structures:

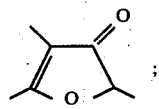

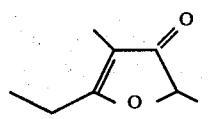

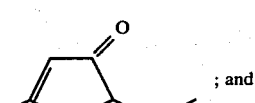 ; and

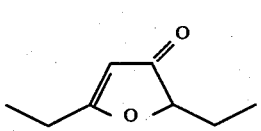

Into a 3 liter reaction flask equipped with mechanical stirrer, condenser, addition funnel and thermometer are placed 500 gram of 2,3-pentane dione. The reaction mass temperature is kept at approximately −5° C. using an isopropanol/dry ice bath. 100 ml of a 10% aqueous KOH solution is then added dropwise over a period of 30 minutes while maintaining the reaction mass temperature at between −5° C. and +6° C. 480 ml of a 20% aqueous KOH solution is then added dropwise over 1½ hours while keeping mass temperature at −5° C.−+6° C. The pH of the resulting slurry is then adjusted to 7 using 80 ml of a 50% H₂SO₄ solution (aqueous) followed by 80 ml concentrated HCl addition. The reaction mass is then steam heated (at 95° C. over a period of 7 hours). The reaction mass is then cooled and the pH of the slurry is adjusted to 7 using 125 ml of 25% NaOH followed by adding 144 grams of sodium chloride. The reaction mass is then extracted with anhydrous diethyl ether (750 ml×1; 500 ml×2; and 250 ml×1). The diethyl ether extracts are combined and washed twice with saturated sodium bicarbonate (250 ml, 200 ml and 100 ml) and 10% sodium carbonate (450 ml×2). The ether extract is then washed with saturated sodium chloride (200 ml×3) and dried over anhydrous sodium sulfate. The concentrated crude obtained (419 grams with solvent) or 326 grams without solvent is then analyzed: GC analysis indicates that this material contains 15% compound having the structure:

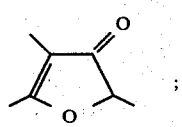

8.5% compound having the structure:

12.5% compound having the structure:

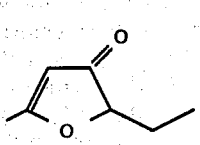

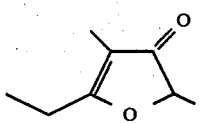

and 7.8% compound having the structure:

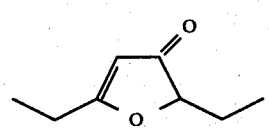

This mixture is hereinafter referred to as mixture "BA".

Another 500 grams of 2,3-propane dione is reacted with KOH in a manner similar to that set forth above as follows: To 500 grams of 2,3-pentane dione 100 ml 10% aqueous KOH is added keeping the reaction temperature at −3° C.−+7° C. 450 ml 20% aqueous KOH is added over a period of 1.5 hours at −3° C.−+7° C. The pH is adjusted to 7 using 80 ml 50% H to a sulfur followed by 80 ml concentrated hydrochloric acid. The reaction mass is steam heated at 95° C. for 7 hours. The slurry is admixed with 75 grams of sodium chloride and extracted with diethyl ether (500 ml×2; 300 ml×1). The ether extract is washed with saturated sodium chloride (250 ml×2) and then washed with 10% Na₂CO₃ (200 ml×3; 150 ml×1). The ether extract is then washed again with saturated sodium chloride (200 ml×2, 150 ml×1) and dried over anhydrous sodium sulfate. The concentrate obtained weighs 327 grams and is analyzed as follows:

20.3% compound having the structure:

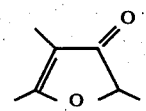

9.2% compound having the structure:

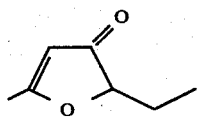

16.7% compound having the structure:

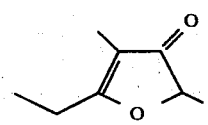

7.8% compound having the structure:

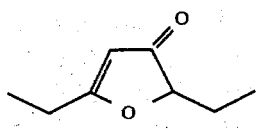

This mixture is hereinafter referred to as mixture "BB".

The combined crudes have a total weight of 800 grams. The combined crudes are then rushed over distilled yielding 13 fractions as follows:

| No. | Vapor Temp. (°C.) | Liquid Temp. (°C.) | Vac. mm.Hg | Weight of Fraction g. |
|---|---|---|---|---|
| 1 | 30–50 | 55–80 | 110 | 5.0 |
| 2 | 50–35 | 80–90 | 110–40 | 10.3 |
| 3 | 75 | 127 | 38 | 10.3 |
| 4 | 94 | 129 | 38 | 6.0 |
| 5 | 97 | 133 | 38 | 15.0 |
| 6 | 99 | 147 | 38 | 76.0 |
| 7 | 107 | 165 | 36 | 60.0 |
| 8 | 121 | 168 | 25 | 32.0 |
| 9 | 124 | 170 | 18 | 42.0 |
| 10 | 130 | 178 | 14 | 23.1 |
| 11 | 134 | 180 | 11 | 29.6 |
| 12 | 137 | 189 | 10 | 25.7 |
| 13 | 140 | 193 | 5 | 27.3 |

Combined fractions 6, 7 and 8 from the rushover are then redistilled yielding the following fractions:

| No. | Vapor Temp. (°C.) | Liquid Temp. (°C.) | Vac mm. | Reflux Ratio | Wt. of Fraction g. |
|---|---|---|---|---|---|
| 1 | 21–48 | 70–88 | 13 | 4:1 | 6.6 |
| 2 | 73 | 88 | 13 | 4:1 | 4.2 |
| 3 | 74 | 88 | 14 | 4:1 | 4.4 |
| 4 | 74 | 89 | 13 | 4:1 | 2.4 |
| 5 | 76 | 89 | 13 | 4:1 | 4.5 |
| 6 | 76 | 89 | 13 | 4:1 | 3.8 |
| 7 | 76 | 89 | 13 | 4:1 | 3.4 |
| 8 | 76 | 89 | 13 | 4:1 | 4.2 |
| 9 | 75 | 89 | 13 | 9:1 | 1.6 |
| 10 | 75 | 90 | 13 | 9:1 | 2.5 |
| 11 | 75 | 90 | 13 | 9:1 | 2.3 |
| 12 | 75 | 90 | 13 | 9:1 | 2.8 |
| 13 | 76 | 90 | 13 | 9:1 | 3.4 |
| 14 | 78 | 92 | 13 | 3:1 | 11.7 |
| 15 | 79 | 92 | 13 | 3:1 | 10.3 |
| 16 | 80 | 93 | 13 | 3:1 | 9.0 |
| 17 | 82 | 96 | 13 | 3:1 | 13.1 |
| 18 | 82 | 96 | 13 | 3:1 | 10.6 |
| 19 | 82 | 98 | 13 | 3:1 | 15.8 |
| 20 | 84 | 112 | 13 | 3:1 | 11.1 |
| 21 | 88 | 145 | 13 | 3:1 | 11.8 |
| 22 | 83 | 250 | 3 | 3:1 | 12.0 |

Fractions 6, 7 and 8, prior to distillation contain 37% compound having the structure:

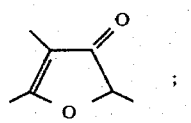

15.9% of compound having the structure:

28.4% of compound having the structure:

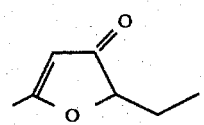

and 15.3% of compound having the structure:

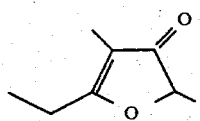

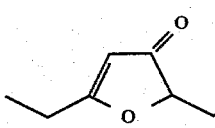

This mixture is hereinafter referred to as mixture "BC".

Figure 1:
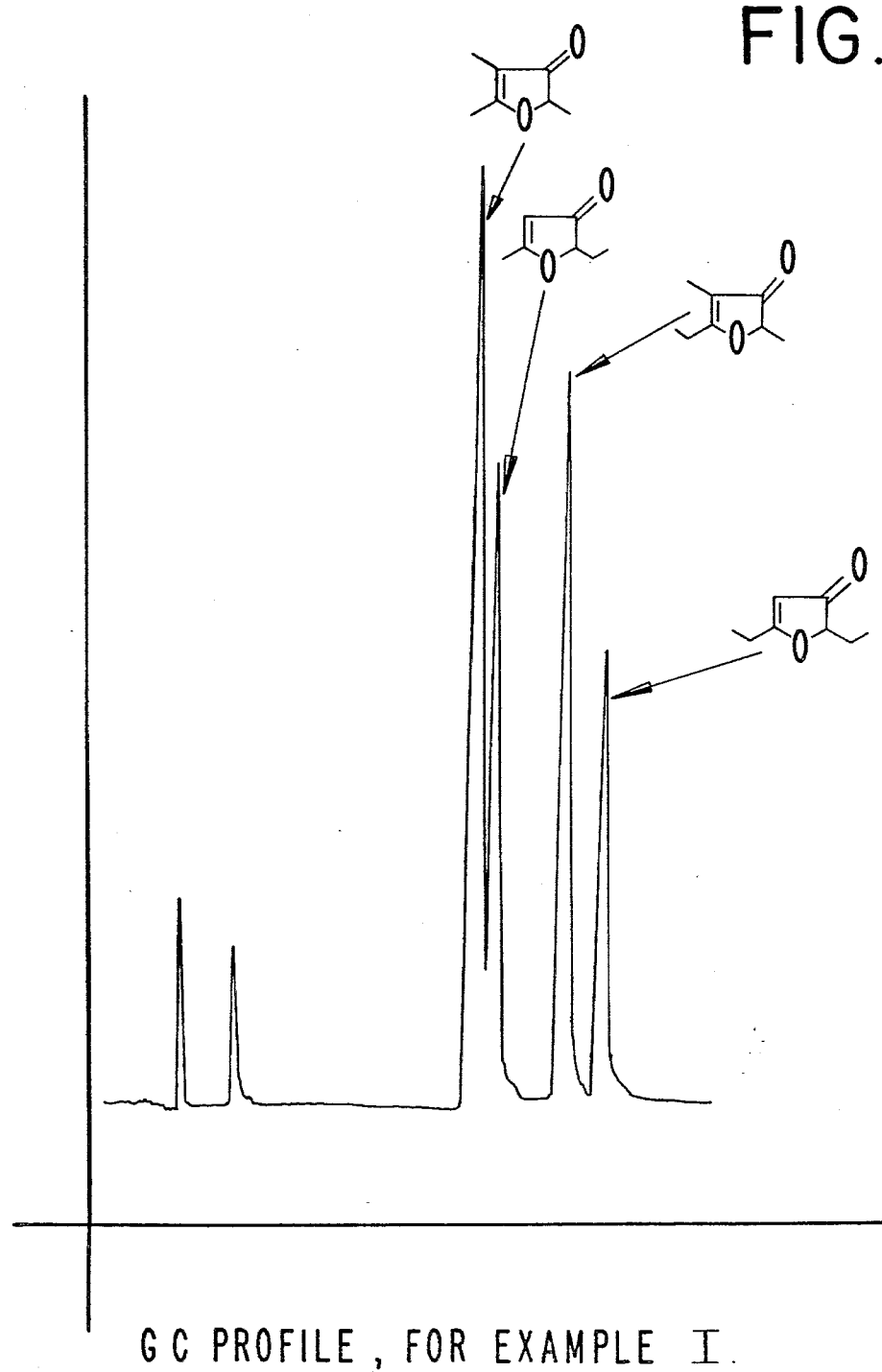
FIG. 1 is the gas chromotograph (GC) profile for the mixture of compounds each of which has the structure.

FIG. 1 is a GC profile of the reaction product of Example I which contains a mixture of compounds having the structures:

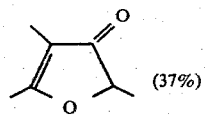 (37%)

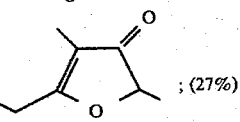 ; (27%)

 ; (15%) and

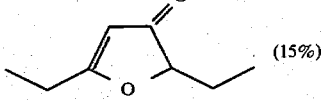 (15%)

having the names, respectively, 2,4,5-trimethyl-2,3-dihydro-3-furanone; 2,4-dimethyl-5-ethyl-2,3-dihydro-3-furanone; 2-ethyl-5-methyl-2,3-dihydro-3-furanone; 2,5-diethyl-2,3-dihydro-3-furanone.

The final distillation is carried out on a Goodloe column from which fractions 6–21 were combined and submitted for evaluation. This material has a sweet, caramel, diacetyl-like, buttery aroma characteristic with sweet, caramel, diacetyl-like, buttery and vanillin flavor characteristics. It is useful in caramel, butterscotch, rum, dairy, vanilla and roasted almond flavors. The level of useage may vary from 0.5 ppm up to 100 ppm with a preferred level of useage at 1–5 ppm.

EXAMPLE II

BASIC CARAMEL FLAVOR FORMULATION

The following caramel flavor formulation is prepared:

| Ingredients | Parts by Weight |
|---|---|
| Palatone | 3 |
| Heliotropine | 2 |
| Cyclotene | 2 |
| Vanillin | 2 |
| Isovaleraldehyde | 1 |
| 5-methyl furfural | 2 |
| Rum ether | 15 |
| Pyruvic acid | 5 |
| Ethyl butyrate | 10 |
| Propylene glycol | 158 |

This basic caramel flavor is divided into five parts. To each of the first four parts, 5% by weight, respectively, of (i) the bulked fractions 3–8 resulting from the rushover distillation of Example I, Part A (mixture "A") or (ii) concentrated crude mixture "BA" resulting from the reaction carried out in Part B of Example I or (iii) concentrated crude mixture "BB" resulting from the reaction carried out in Part B of Example I or (iv) mixture "BC", bulked fractions 6–8 resulting from the fractional distillation described in Part B of Example I is added.

To the fifth part, nothing is added.

All five flavors, (i)–(iv) are tasted at the rate of 20 ppm in water by a bench panel of three flavor experts. All three members of the bench panel state that the formulations containing one of said mixtures "A" prepared according to Example I, Part A or any of mixtures "BA", "BB" or "BC" has a more characteristic caramel, burnt sugar aroma and taste. In addition, there is a buttery mouthfeel in the flavor formulation containing any of the mixtures prepared according to Example I, Part A (mixture "A") or mixtures "BA", "BB" or "BC". Therefore, the flavors containing mixtures prepared according to Example I, Part A, (mixture "A") of any of mixtures "BA", "BB", or "BC" or unanimously preferred as having a better caramel character.

EXAMPLE III

ISOLATION OF 2,4,5-TRIMETHYL-3(2H)FURANONE FROM BACON FLAVOR 500 pounds of Oscar Mayer bacon was firstly ground to 3/16" mesh and each batch (100 pounds) was cooked in steam jacked kettle from 50° F. to 350° F. over a period of one hour. Slurry obtained from 5 batches was about 300 pounds, about 200 pounds of water was lost during process. The slurry was subjected to vacuum steam distillation in ten charges and each charge is distilled in two passes. The apparatus is set forth in FIG. 10. The resulting distillate was saturated with NaCl and subjected to continuous extraction and concentrated to 1 liter.

A small portion is taken to estimate the total volatile weight which is approximately 3 grams. The total volatiles are chemically separated using the separation scheme as set forth in FIG. 11. 400 mg of phenolic fraction obtained is fractionated on a silicon dioxide column (10% deactivated silica, 14 grams, column volume equals 30 ml/250 mm × 12 mm) using isopentane and then varying mixtures (1%–100%) of diethyl ether in isopentane.

The fraction containing the 2,4,5-trimethyl-3(2H)furanone is subjected to GLC analysis conditions: stainless steel carbowax 20M column, ⅛ inch × 10 ft., 60°–220° C. at 4° C./minute). The GLC chromatogram is set forth in FIG. 12. The 2,4,5-trimethyl-3(2H) furanone synthesized according to Example I, Part A has a GLC profile as set forth in FIG. 13. The GLC profile retention time for said furnaone in FIG. 13 is identical to the GLC profile retention time of the furanone isolated from fried bacon flavor. The IR spectrum for the isolated furanone is set forth in FIG. 14. The NMR spectrum for the isolated furanone is set forth in FIG. 15. The mass spectrum for the isolated furanone is set forth in FIG. 16.

EXAMPLE IV

To a standard custard mix (JELL-O ®-manufactured by the General Foods Corporation of White Plains, New York 10625) brand of Americana Golden Egg Custard mix three ounce package is added 100 ppm of mixture "A" prepared according to Example I, Part A. The resulting custard mix is blended with two cups of milk in a sauce pan and one additional egg yolk. The mixture is quickly brought to a boil with constant stirring. The custard is poured into dessert dishes and sprinkled with nutmeg. The resulting material is then chilled until set (approximately one hour). The resulting dessert has a much more intense caramel-like flavor and aroma than those custard dessert prepared without the use of mixture "A".

When mixtures "BA", "BB" or "BC" are substituted for mixture "A", the same results are attained; that is, a stronger intense pleasant caramel aroma and taste is achieved which is not achieved at all when either of mixtures "BA", "BB" or "BC" are omitted therefrom.

EXAMPLE V

At the rate of 50 ppm to MY-T FINE ® Pudding and Pie Filling/Butterscotch (manufactured by the RJR Foods, Inc. of Winston-Salem, North Carolina 27102) is added in the alternative mixtures "A", "BA", "BB" and "BC".

In each of the cases where a mixture is "A", "BA", "BB" and "BC" are used, the contents of a 3.25 ounce package of butterscotch pudding is emptied into a sauce pan. Two cups of milk are added. The resulting mixture is cooked over medium heat with constant stirring until the pudding just begins to boil. The pudding melt is poured into four half cups and chilled. The resulting butterscotch puddings have an excellent caramel nuance which is highly intense and pleasant. This caramel nuance is essentially missing from the butterscotch pudding prepared without the use of either of mixtures "A", "BA", "BB" and "BC".

EXAMPLE VI

The taste and aroma of solutions of equal intensity of test compositions as set forth below are compared as follows:

| Solution | Evaluation |
|---|---|
| (i) Mixtures "A", "BA", "BB" and "BC" at 2 ppm | A sweet, caramel, diacetyl-like, buttery aroma character and a sweet, caramel, diacetyl, buttery and vanillin flavor characteristics of high intensity having a potential use in caramel, butterscotch, rum, dairy, vanilla and roasted almond-flavored foodstuffs. Much more intense and longer lasting than the compound having the structure: |

| Solution | Evaluation |
|---|---|
| (ii) Compound having the structure:<br>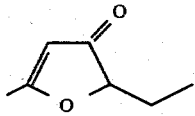 | A buttery, brown sugar, pineapple-like, caramel aroma and taste at 10 ppm (intensity 0.2 that of mixtures "A", "BA", "BB" and "BC". | are comparatively evaluated in a caramel formulation as follows:

| Ingredients | Parts by Weight |
|---|---|
| Palatone | 3 |
| Heliotropine | 2 |
| Cyclotene | 2 |
| Vanillin | 2 |
| Isovaleraldehyde | 1 |
| 5-Methyl furfural | 2 |
| Rum ether | 15 |
| Pyruvic acid | 5 |
| Ethyl butyrate | 10 |
| Propylene glycol | 158 | then the same results occur. That is, the intensity of the caramel note particularly is five times that when using the mixture "A", "BA", "BB" and "BC" rather than the compound having ehs structure:

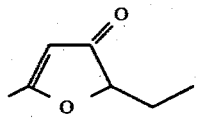

It is our conclusion based on the results set forth in the immediately preceeding paragraph that mixtures "A", "BA", "BB" and "BC" compared with the compound having the structure:

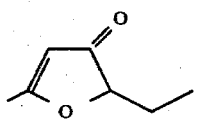

has unobvious, unexpected and advantageous properties, particularly in caramel, butterscotch, rum, dairy, vanilla and roasted almond flavored foodstuffs. Furthermore, the effect of using the mixture of the four compounds in flavors is a synergistic effect unexpected and unobvious within the standards of psychophysical measurement as set forth in the paper by Moskowitz et al at page 91 of Vol. 30, No., Journal of the Society of Cosmetic Chemists.

What is claimed is:

1. A process for augmenting or enhancing the taste or aroma of a caramel, butterscotch, rum, dairy,, vanilla or roasted almond-flavored foodstuff comprising the step of adding to said foodstuff from about 0.1 ppm up to about 50 ppm by weight of said foodstuff of a mixture of dialkyl and trialkyl dihydrofuranones having the structures:

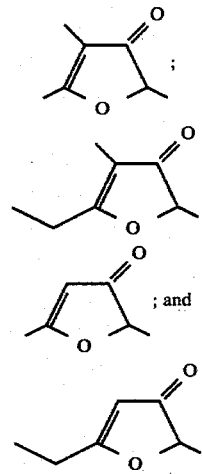

wherein the weight percentage ranges in said dihydrofuranones in said mixture is from about 10% up to about 40% by weight of the compound having the structure:

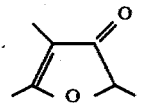

from about 5% up to about 20% of the compound having the structure:

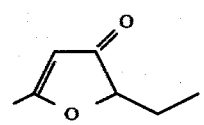

from about 10% up to about 30% of the compound having the structure:

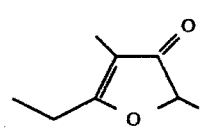

and from about 5% up to about 20% of the compound having the structure:

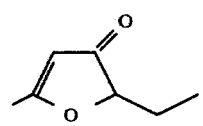

2. A flavor augmenting or enchancing composition for augmenting or enhancing the caramel, butterscotch, rum, diary, vanilla or roasted almond flavor of foodstuffs comprising from about 0.1% up to 15% by weight based on the total weight of flavoring composition of a mixture of dialkyl and trialkyl dihydrofuranones having the structures:

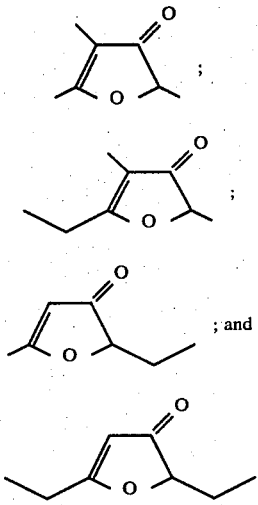

and the remainder of said composition being at least one adjuvant selected from the group consisting of:
Eugenol
Guaiacol
Vanillin
Sucrose
Heliotropin
Ethyl Vanillin
Maltol
Ethyl Maltol
Cyclotene
Ethyl Cyclotene
Methyl Cyclopentenolone Butyrate
2,5-Dimethyl-4-Hydroxy-3(2H)-Furanone
Isovaleraldehyde
5-Methyl Furfural
Rum Ether Pyruvic acid; and
Ethyl Butyrate wherein the weight percentage ranges of said dihydrofuranones in said mixture is from about 10% up to about 40% by weight of the compound having the structure:

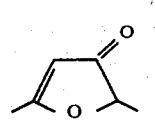

from about 5% up to about 20% of the compound having the structure:

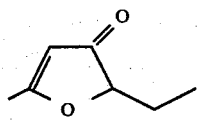

from about 10% up to about 30% of the compund having the structure:

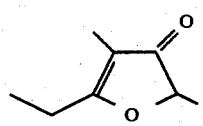

and from about 5% up to about 20% of the compound having the structure:

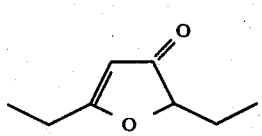

* * * * *